US007008433B2

(12) United States Patent
Voellmicke et al.

(10) Patent No.: US 7,008,433 B2
(45) Date of Patent: Mar. 7, 2006

(54) VERTEBROPLASTY INJECTION DEVICE

(75) Inventors: John C. Voellmicke, Providence, RI (US); Paul J. Mraz, Boston, MA (US); Robert Sommerich, Norton, MA (US); John Buonanno, Bristol, RI (US); Francis Peterson, Prescott, WI (US); Todd Bjork, River Falls, WI (US); Mark Duffy, Plainville, MA (US)

(73) Assignee: DePuy Acromed, Inc., Raynham, MA (US)

( * ) Notice: Subject to any disclaimer, the term of this patent is extended or adjusted under 35 U.S.C. 154(b) by 652 days.

(21) Appl. No.: 09/784,383

(22) Filed: Feb. 15, 2001

(65) Prior Publication Data

US 2002/0156483 A1    Oct. 24, 2002

(51) Int. Cl.
    *A61B 2/00*    (2006.01)
(52) U.S. Cl. .................. 606/93; 222/256; 222/380
(58) Field of Classification Search .................. 606/92, 606/93, 94; 222/256, 380
    See application file for complete search history.

(56) References Cited

U.S. PATENT DOCUMENTS

| | | |
|---|---|---|
| 1,894,274 A | 1/1933 | Jacques |
| 2,123,712 A | 7/1938 | Clark |
| 2,394,488 A | 2/1946 | Rotter et al. |
| 2,425,867 A | 8/1947 | Davis |
| 2,435,647 A | 2/1948 | Engseth |
| 2,497,762 A | 2/1950 | Davis |
| 2,521,569 A | 9/1950 | Davis |
| 3,572,556 A | 3/1971 | Pogacar |
| 3,796,303 A | 3/1974 | Abbel-Coche |
| 3,850,158 A | 11/1974 | Elias et al. |
| 4,077,494 A | 3/1978 | Spaude et al. |
| 4,146,334 A | 3/1979 | Farrell |
| 4,168,787 A | 9/1979 | Stamper |
| 4,239,113 A | 12/1980 | Gross et al. |
| 4,268,639 A | 5/1981 | Seidel et al. |
| 4,277,184 A | 7/1981 | Solomon |
| 4,298,144 A | 11/1981 | Pressl |
| 4,338,925 A | 7/1982 | Miller |
| 4,341,691 A | 7/1982 | Anuta |
| 4,359,049 A | 11/1982 | Redl et al. |
| 4,373,217 A | 2/1983 | Draenert |
| 4,403,989 A | 9/1983 | Christensen et al. |
| 4,404,327 A | 9/1983 | Crugnola et al. |
| 4,405,249 A | 9/1983 | Scales |
| 4,487,602 A | 12/1984 | Christensen et al. |
| 4,503,169 A | 3/1985 | Randklev |
| 4,543,966 A | 10/1985 | Islam et al. |
| 4,546,767 A | 10/1985 | Smith |
| 4,576,152 A | 3/1986 | Muller et al. |
| 4,588,583 A | 5/1986 | Pietsch et al. |

(Continued)

FOREIGN PATENT DOCUMENTS

DE    2947875 A1    4/1981

(Continued)

OTHER PUBLICATIONS

Timothy J. Kaufmann et al.; Age of Fracture and Clinical Outcomes of Percutaneous Vertebroplasty; American Journal of Neuroradiology; Nov./Dec. 2001; vol. 22; pp. 1860-1863;22.

(Continued)

*Primary Examiner*—Ralph A. Lewis
(74) *Attorney, Agent, or Firm*—Thomas M. DiMauro

(57) ABSTRACT

This invention relates to a mixing and delivery device suitable for delivering injectable biomaterials, and to preferred bone cement formulations.

1 Claim, 12 Drawing Sheets

U.S. PATENT DOCUMENTS

| | | |
|---|---|---|
| 4,593,685 A | 6/1986 | McKay et al. |
| 4,595,006 A | 6/1986 | Burke et al. |
| 4,600,118 A | 7/1986 | Martin |
| 4,642,099 A | 2/1987 | Phillips et al. |
| 4,651,904 A | 3/1987 | Schuckmann |
| 4,664,298 A | 5/1987 | Shew |
| 4,664,655 A | 5/1987 | Orentreich et al. |
| 4,668,295 A | 5/1987 | Bajpai |
| 4,670,008 A | 6/1987 | Von Albertini |
| 4,671,263 A | 6/1987 | Draenert |
| 4,676,781 A | 6/1987 | Phillips et al. |
| 4,714,721 A | 12/1987 | Franek et al. |
| 4,717,383 A | 1/1988 | Phillips et al. |
| 4,722,948 A | 2/1988 | Sanderson |
| 4,735,616 A | 4/1988 | Eibl et al. |
| 4,758,234 A | 7/1988 | Orentreich et al. |
| 4,782,118 A | 11/1988 | Fontanille et al. |
| 4,791,150 A | 12/1988 | Braden et al. |
| 4,804,023 A | 2/1989 | Frearson |
| 4,813,870 A | 3/1989 | Pitzen et al. |
| 4,826,053 A | 5/1989 | Keller |
| 4,830,227 A | 5/1989 | Ball et al. |
| 4,837,279 A | 6/1989 | Arroyo |
| 4,892,231 A | 1/1990 | Ball |
| 4,910,259 A | 3/1990 | Kindt-Larsen et al. |
| 4,927,866 A | 5/1990 | Purrmann et al. |
| 4,946,077 A | 8/1990 | Olsen |
| 4,966,601 A | 10/1990 | Draenert |
| 4,969,888 A | 11/1990 | Scholten et al. |
| 4,973,334 A | 11/1990 | Ziemann |
| 4,978,336 A | 12/1990 | Capozzi et al. |
| 4,994,065 A | 2/1991 | Gibbs et al. |
| 5,022,563 A | 6/1991 | Marchitto et al. |
| 5,049,157 A | 9/1991 | Mittelmeier et al. |
| 5,071,040 A | 12/1991 | Laptewicz, Jr. |
| 5,108,403 A | 4/1992 | Stern |
| 5,108,404 A | 4/1992 | Scholten et al. |
| 5,114,240 A | 5/1992 | Kindt-Larsen et al. |
| 5,125,971 A | 6/1992 | Nonami et al. |
| 5,141,496 A | 8/1992 | Dalto et al. |
| 5,181,918 A | 1/1993 | Brandhorst et al. |
| 5,190,191 A | 3/1993 | Reyman |
| 5,217,147 A | 6/1993 | Kaufman |
| 5,242,983 A | 9/1993 | Kennedy et al. |
| 5,252,301 A | 10/1993 | Nilson et al. |
| 5,258,420 A | 11/1993 | Posey-Dowty et al. |
| 5,264,215 A | 11/1993 | Nakabayashi et al. |
| 5,275,214 A | 1/1994 | Rehberger |
| 5,276,070 A | 1/1994 | Arroyo |
| 5,277,339 A | 1/1994 | Shew et al. |
| 5,279,555 A | 1/1994 | Lifshey |
| 5,328,262 A | 7/1994 | Lidgren et al. |
| 5,331,972 A | 7/1994 | Wadhwani et al. |
| 5,334,626 A | 8/1994 | Lin |
| 5,336,699 A | 8/1994 | Cooke et al. |
| 5,344,232 A | 9/1994 | Nelson et al. |
| 5,368,046 A | 11/1994 | Scarfone et al. |
| 5,370,221 A | 12/1994 | Magnusson et al. |
| 5,372,583 A | 12/1994 | Roberts et al. |
| 5,374,427 A | 12/1994 | Stille et al. |
| 5,385,081 A | 1/1995 | Sneddon |
| 5,385,566 A | 1/1995 | Ullmark |
| 5,398,483 A | 3/1995 | Smith et al. |
| 5,415,474 A | 5/1995 | Nelson et al. |
| 5,431,654 A | 7/1995 | Nic |
| 5,450,924 A | 9/1995 | Tseng |
| 5,456,267 A | 10/1995 | Stark |
| 5,468,245 A | 11/1995 | Vargas, III |
| 5,482,187 A | 1/1996 | Poulsen et al. |
| 5,492,247 A | 2/1996 | Shu et al. |
| 5,494,349 A | 2/1996 | Seddon |
| 5,501,520 A | 3/1996 | Lidgren et al. |
| 5,512,610 A | 4/1996 | Lin |
| 5,549,380 A | 8/1996 | Lidgren et al. |
| 5,549,381 A | 8/1996 | Hays et al. |
| 5,551,778 A | 9/1996 | Hauke et al. |
| 5,558,136 A | 9/1996 | Orrico |
| 5,578,035 A | 11/1996 | Lin |
| 5,586,821 A | 12/1996 | Bonitati et al. |
| 5,588,745 A | 12/1996 | Tanaka et al. |
| 5,624,184 A | 4/1997 | Chan |
| 5,634,880 A | 6/1997 | Feldman et al. |
| 5,638,997 A | 6/1997 | Hawkins et al. |
| 5,660,186 A | 8/1997 | Bachir |
| 5,681,317 A | 10/1997 | Caldarise |
| 5,698,611 A | 12/1997 | Okada et al. |
| 5,718,707 A * | 2/1998 | Mikhail .................... 606/94 |
| 5,763,092 A | 6/1998 | Lee et al. |
| 5,779,356 A | 7/1998 | Chan |
| 5,795,922 A | 8/1998 | Demian et al. |
| 5,800,169 A | 9/1998 | Muhlbauer |
| 5,824,087 A | 10/1998 | Aspden et al. |
| 5,826,753 A | 10/1998 | Fehlig et al. |
| 5,829,875 A | 11/1998 | Hagel et al. |
| 5,876,116 A | 3/1999 | Barker et al. |
| 5,884,818 A | 3/1999 | Campbell |
| 5,893,488 A | 4/1999 | Hoag et al. |
| 5,902,839 A | 5/1999 | Lautenschlager et al. |
| 5,918,702 A | 7/1999 | Cheng et al. |
| 5,918,770 A | 7/1999 | Camm et al. |
| 5,925,051 A | 7/1999 | Mikhail |
| 5,928,239 A | 7/1999 | Mirza |
| 5,931,347 A | 8/1999 | Haubrich |
| 5,954,671 A | 9/1999 | O'Neill |
| 5,954,728 A | 9/1999 | Heller et al. |
| 5,961,211 A | 10/1999 | Barker et al. |
| 5,968,999 A | 10/1999 | Ramp et al. |
| 5,993,535 A | 11/1999 | Sawamura et al. |
| 5,997,544 A | 12/1999 | Nies et al. |
| 6,004,325 A | 12/1999 | Vargas, III |
| 6,007,496 A | 12/1999 | Brannon |
| 6,017,349 A | 1/2000 | Heller et al. |
| 6,019,765 A | 2/2000 | Thornhill et al. |
| 6,019,776 A | 2/2000 | Preissman et al. |
| 6,020,396 A | 2/2000 | Jacobs |
| 6,033,105 A | 3/2000 | Barker et al. |
| 6,033,411 A | 3/2000 | Preissman |
| 6,040,408 A | 3/2000 | Koole |
| 6,042,262 A | 3/2000 | Hajianpour |
| 6,049,026 A | 4/2000 | Muschler |
| 6,075,067 A | 6/2000 | Lidgren |
| 6,080,579 A | 6/2000 | Hanley, Jr. et al. |
| 6,080,801 A | 6/2000 | Draenert et al. |
| 6,116,773 A | 9/2000 | Murray |
| 6,120,174 A | 9/2000 | Hoag et al. |
| 6,132,396 A | 10/2000 | Antanavich et al. |
| 6,139,509 A | 10/2000 | Yuan et al. |
| 6,142,998 A | 11/2000 | Smith et al. |
| 6,149,655 A | 11/2000 | Constantz et al. |
| 6,160,033 A | 12/2000 | Nies |
| 6,176,607 B1 | 1/2001 | Hajianpour |
| 6,210,031 B1 | 4/2001 | Murray |
| 6,214,012 B1 | 4/2001 | Karpman et al. |
| 6,217,581 B1 | 4/2001 | Tolson |
| 6,221,029 B1 | 4/2001 | Mathis et al. |
| 6,231,615 B1 | 5/2001 | Preissman |
| 6,235,043 B1 | 5/2001 | Reiley et al. |
| 6,238,399 B1 | 5/2001 | Heller et al. |
| 6,241,734 B1 | 6/2001 | Scribner et al. |
| 6,254,268 B1 | 7/2001 | Long |
| 6,264,618 B1 | 7/2001 | Landi et al. |
| 6,264,660 B1 | 7/2001 | Schmidt et al. |
| 6,273,916 B1 | 8/2001 | Murphy |
| 6,309,395 B1 | 10/2001 | Smith et al. |

| | | | |
|---|---|---|---|
| 6,309,420 B1 | 10/2001 | Preissman | |
| 6,312,149 B1 | 11/2001 | Sjovall et al. | |
| 6,348,055 B1 | 2/2002 | Preissman | |
| 6,402,758 B1 * | 6/2002 | Tolson | 606/94 |
| 6,439,439 B1 * | 8/2002 | Rickard et al. | 222/391 |
| 2001/0034527 A1 | 10/2001 | Scribner et al. | |
| 2002/0010471 A1 | 1/2002 | Wironen et al. | |
| 2002/0010472 A1 | 1/2002 | Kuslich et al. | |
| 2002/0013553 A1 | 1/2002 | Pajunk et al. | |

FOREIGN PATENT DOCUMENTS

| | | |
|---|---|---|
| DE | 3443167 A1 | 6/1986 |
| DE | 3730298 A1 | 2/1990 |
| DE | 4016135 A1 | 3/1992 |
| EP | 0190504 A2 | 3/1986 |
| EP | 0301759 A2 | 7/1988 |
| EP | 0242672 A2 | 9/1989 |
| EP | 0425200 A1 | 10/1990 |
| EP | 0511868 A2 | 4/1992 |
| FR | 2606282 A1 | 5/1988 |
| FR | 2690332 A | 10/1993 |
| GB | 2156824 A | 10/1985 |
| JP | 10146559 | 6/1998 |
| WO | WO 99/18866 A1 | 4/1999 |
| WO | WO 99/37212 A1 | 7/1999 |
| WO | WO 99/49819 A1 | 10/1999 |
| WO | WO 00/56254 A1 | 9/2000 |
| WO | WO 01/76514 A2 | 10/2001 |
| WO | WO 02/00143 A1 | 1/2002 |

OTHER PUBLICATIONS

Paul F. Heini et al.,; Augmentation of mechanical properties in osteoporatic vertebral bones—a biomechanical investigation of vertebroplasty efficacy with different bone cements; EUR Spine Journal; Jan. 27, 2001; vol. 10; pp. 164-171; Springer-Verlag 2001.

Stephen M. Belkoff, PHD et al.; The Biomechanics of Vertebroplasty, The Effect of Cement Volume on Mechanical Behavior, SPINE vol. 26; No. 14, Nov. 14, 2001; pp. 1537-1541;©2001, Lippincott Williams & Wilkins, Inc.

Dr. Klaus-Dieter Kuhn; Bone Cements, Up-to-Date Comparison of Physical and Chemical Properties of Commercial Materials; ©Springer-Verlag Heidelberg 2000; Germany.

Johnson & Johnson Orthopaedics; The CEMVAC Method; Raynham, MA.

J. R. De Wijn et al.; Characterization of Bone Cements; The Institute of Dental Materials Science and Technology and the Department of Orthopaedics, Catholic University, Nijmegen, The Netherlands; 1975; 46, pp. 38-51.

Afshin Gangi, MD, PHD, et al.; Computed Tomography (CT) and Flouroscopy-guided Vertebroplasty: Results and Complications in 187 Patients; Seminars in Interventional Radiology, vol. 16, No. 2, 1999; pp. 137-142;©1999 Thieme Medical Publishers, Inc., New York, NY.

Afshin Gangi, MD et al.; CT-guided Interventional Procedures for Pain Management in the Lumbosacral Spine; Radiographics 1998; 18:621-633.

Kyung Sik Ryu, MD, et al. Dose-dependent epidural leakage of polymethylmethacrylate after percutaneous vertebroplasty in patients with osteoporotic vertebral compression fractures; J. Neurosurgery: Spine/vol. 96/Jan., 2002; pp. 56-61.

L. E. Jasper, et al.; The Effect of Monomer-to-Powder Ratio on the Material Properties of Cranioplastic; Bone, vol. 25, No. 2 Supplement, Aug. 1999:27S-29S; ©1999 Elsevier Science Inc.

Steven P. Combs, MD et al.; The effects of Barium Sulfate on the Polymerization Temperature and Shear Strength of Surgical Simplex P; Clinical Orthopaedics and Related Research; Jun. 4, 1979; pp. 287-291; © J. B. Lippincott Co.

J. A. Wimhurst; et al.; The effects of particulate bone cements at the bone-implant interface; The Journal of Bone & Joint Surgery; pp. 588-592; © 2001 British Editorial Society of Bone and Joint Surgery.

Stephen M. Belkoff et al.; An Ex Vivo Biomechanical Evaluation of a Hydroxyapatite Cement for use with Kyphoplasty; American Journal of Neuroradiology, vol. 22, pp. 1212-1216; ©2001.

Stephen M. Belkoff, PHD et al.; An Ex Vivo Biomechanical Evaluation of an Inflatable Bone Tamp Used in the Treatment of Compression Fracture; SPINE, vol. 26, No. 2, pp. 151-156; ©2001, Lippincott Williams & Wilkins, Inc.

Parallax Medical, Inc.; Exflow Cement Delivery System; May 16, 2000.

S. M. Belkoff et al.; An In Vitro Biomechanical Evaluation of Bone Cements Used in Percutaneous Vertebroplasty; Bone, vol. 25, No. 2 Supplement; Aug. 1999; pp. 23S-26S; ©1999 Elsevier Science Inc.

J. A. Wimhurst et al.; Inflammatory responses of human primary macrophages to particulate bone cements in vitro; The Journal of Bone & Joint Surgery; vol. 83-B; pp. 278-282; ©2001 British Editorial Society of Bone and Joint Surgery.

I. H. Lieberman, MD et al.; Initial Outcome and Efficacy of "Kyphoplasty" in the Treatment of Painful Osteoporotic Vertebral Compression Fractures; SPINE vol. 26, No. 14, pp. 1631-1638; ©2001.

Kyphon Medical Professionals; KyphXProducts; Nov. 8, 2001.

F. Grados et al.; Long-term observations of vertebral osteoporotic fractures treated by percutaneous vertebroplasty; Rheumatology 2000; vol. 39, pp. 1410-1414; ©2000; British Society of Rheumatology.

Stephen R. Garfin, MD et al.; New Technologies in Spine, Kyphoplasty and Vertebroplasty for the Treatment of Painful Osteoporotic Compression Fractures; SPINE vol. 26, No. 14, pp. 1511-1515; ©2001, Lippincott Williams & Wilkins, Inc.

Mary E. Jensen et al.; Percutaneous Polymethylmethacrylate Vertebroplasty in the Treatment of Osteoporotic Vertebral Body Compression Fractures: Technical Aspects; AJNR 18: 1897-1904; Nov. 1997 ©American Society of Neuroradiology.

Arun Paul Amar, MD et al.; Percutaneous Transpedicular Polymethylmethacrylate Vertebroplasty for the Treatment of Spinal Compression Fractures; Neurosurgery, vol. 49, No. 5, pp. 1105-1115, Nov. 2001.

P. F. Heini; Percutaneous transpedicular vertebroplasty with PMMA: operative technique and early results, A prospective study for the treatment of osteoporotic compression fractures; Eur Spine Journal 9:445-450, ©Springer-Verlag 2000.

John M. Mathis et al.; Percutaneous Vertebroplasty: A Developing Standard of Care for Vertebral Compression Fractures; AJNR American Journal of Neuroradiology 22: 373-381, Feb. 2001; ©American Society of Neuroradiology.

Afshin Gangi; Percutaneous Vertebroplasty Guided by a Combination of CT and Fluoroscopy; AJNR 15:83-86, Jan. 1994; ©American Society of Neuroradiology.

John D. Barr, MD et al.; Percutaneous Vertebroplasty for Pain Relief and Spinal Stabilization; SPINE vol. 25, No. 8, pp. 923-928; ©2000, Lippincott Williams & Wilkins, Inc.

Herve Deramond, MD et al.; Percutaneous Vertebroplasty with Polymethylmethacrylate, Technique Indications, and Results; Interventional Procedures in Musculoskeletal Radiology I, Radiologic Clinics of North America, vol. 36, No. 3, May 1988.

Imad Al-Assir et al., Percutaneous Vertebroplasty: A Special Syringe for Cement Injection; AJNR American Journal of Neuroradiology 21: 159-161, Jan. 2000; ©American Society of Neuroradiology.

Anne Cotton, MD et al; Percutaneous Vertebroplasty: State of the Art; Scientific Exhibit; RadioGraphics 1998; 18:311-320; ©RSNA, 1998.

Mary E. Jensen, MD et al.; Percutaneous Vertebroplasty in the Treatment of Osteoporotic Compression Fractures; Spine Interventions, Neuroimaging Clinics of North America, vol. 10, No. 3, Aug. 2000, pp. 547-568.

Bernard Padovani et al.; Pulmonary Embolism Caused by Acrylic Cement: A Rare Complication of Percutaneous Vertebroplasty; AJNR American Journal of Neuroradiology vol. 20, pp. 375-377, Mar. 1999; ©American Society of Neuroradiology.

Tilak M. Shah; Radiopaque Polymer Formulations for Medical Devices; Medical Plastics and Biomaterials Special Section; Medical Device & Diagnostic Industry, Mar. 2000; pp. 102-111.

J. R. Dean et al.; The Strengthening Effect of Percutaneous Vertebroplasty; Clinical Radiology, 55; pp. 471-476; ©2000 The Royal College of Radiologists.

H. Deramond et al.; Temperature Elevation Caused by Bone Cement Polymerization During Vertebroplasty; BONE vol. 25, No. 2 Supplement, Aug. 1999, pp. 17S-21S; ©1999 Elsevier Science Inc.

Cristiana Vasconcelos MD; Transient Arterial Hypotension Induced by Polymethylmethacrylated Injection during Percutaneous Vertebroplasty; Letter to the Editor; JVIR, Aug. 2001.

Paul F. Heini, M.D. et al.; The Use of a Side-Opening Injection Cannula in Vertebroplasty, A Technical Note; SPINE vol. 27, No. 1, pp. 105-109; ©2002, Lippincott Williams & Wilkins, Inc.

Richard D. Fessler, MD et al.; Vertebroplasty; Neurosurgical Operative Atlas, vol. 9, pp. 233-241; ©2000 The American Association of Neurological Surgeons.

James P. O'Brien et al.; Vertebroplasty in Patients with Severe Vertebral Compression Fractures: A Technical Report; AJNR American Journal of Neuroradiology, vol. 21; pp. 1555-1558, Sep. 2000; ©American Society of Neuroradiology.

* cited by examiner

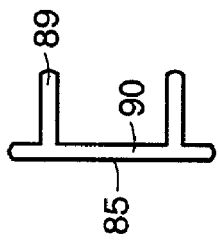
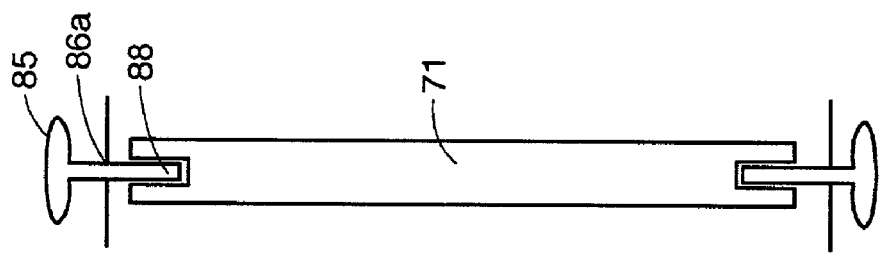
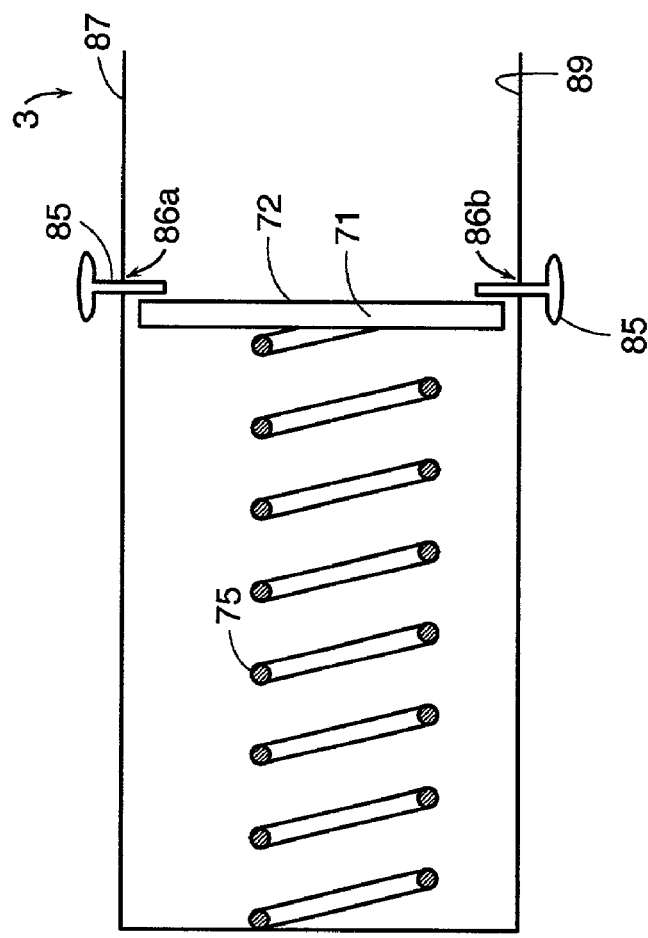

VERTEBROPLASTY INJECTION DEVICE

BACKGROUND OF THE INVENTION

In vertebroplasty, the surgeon seeks to treat a compression fracture of a vertebra by injecting bone cement such as PMMA into the fracture. In one clinical report, Jensen et al., *AJNR:* 18 Nov. 1997, Jensen describes mixing two PMMA precursor components (one powder and one liquid) in a dish to produce a viscous bone cement; filling 10 ml syringes with this cement, injecting it into smaller 1 ml syringes, and finally delivering the mixture into the desired area of the vertebral body through needles attached to the smaller syringes.

Although this procedure has found success, it has also met with some problems. For example, Jensen reports that the open-air mixing of the precursor materials produces problematic fumes. Also, when the plastic plunger in a 1 mm syringe is pressed against the viscous cement in the syringe barrel, the appreciable resistance of the cement to this pressure may cause the relatively thin plunger rod to collapse. To minimize this danger, only about half of the syringe barrel is typically filled with cement. Although this precaution enhances the feasibility of the procedure, it requires loading twice as many syringes, thereby increasing the total time of the procedure.

In addition, the pressures which can be generated by manual operation of 1 ml syringes are fairly low. Referring now to FIG. 7, the pressure generated in a fluid within a conventional syringe S is governed by the equation P=F/A, wherein:

P=the pressure at the cement delivery opening O,
A=the cross-sectional area of the disc D, and
F=the force applied to the handle H in a direction normal to disc D.

Since about 10–15 pounds of force (~44–66 N) is typically generated by manually pressing handle H, and the disc area A of a typical 1 ml syringe is about 0.025 in$^2$ (~16.129 mm$^2$), the pressure P available for injecting the bone cement is only about 400–600 psi (~2.75–4.13 MPa). In vertebroplasty performed with these methods, a pressure of at least about 1000 psi (~6.9 MPa) is desirable, with a pressure of about 2000 psi (~13.78 MPa) being more preferable.

WO 99/49819 ("Preismann") recognized the problem of low delivery pressures in conventional syringes and suggested using a screw-type plunger in a single injection chamber. Although Preismann's screw-type plunger provides more pressure per unit force than the conventional plunger of FIG. 7, it nonetheless requires a cross-sectional area A of about 0.5 in.$^2$ (322 mm$^2$) in order to deliver 2000 psi (~13.78 MPa), and so a chamber capable of delivering 20 cc of bone cement would need to be about 6.22 inches (158 mm) in length. Since this device would likewise require a screw-type plunger of equal length, the total length of the device with the plunger extend would be at least about 12.44 inches (63.5 mm), which is fairly long for a surgical setting. One apparent commercial embodiment of Preismann uses an injection chamber having a length of about 2.5 inches and holds only about 8 cc of bone cement. In addition, Preismann only discloses a delivery system. The user must still mix the two bone cement precursors outside the delivery system, and then transfer the mixed cement to the delivery system.

U.S. Pat. No. 5,252,301("Nilson") discloses a bone cement delivery apparatus wherein the two bone cement precursors are mixed within the injection chamber, thereby solving the fume and transfer problem. However, Nilson discloses a conventional delivery system having a conventional plunger in a single chamber for delivering the bone cement, and so does not provide high pressure delivery.

There are a number of gun-type injectors which seek to use the mechanical advantage of a lever to deliver high pressure fluids from a chamber into the patient. See, for example, U.S. Pat. No. 4,338,925. However, in order to provide pressures of about 2000 psi via a conventional 11.4 cm$^2$ (1.77 inches$^2$) disc in a conventional single chamber device used in orthopaedic applications, the mechanical advantage would have to be very high.

U.S. Pat. No. 5,190,191 ("Reyman") discloses a dual chamber delivery device intended to deliver contraceptive fluid, wherein the fluid is first transferred from a large reservoir into a smaller delivery chamber and then delivered from the delivery chamber by means of a conventional syringe-type plunger. As fluid is delivered via pressure developed by a conventional plunger, this device suffers from the same low pressure deliveries experienced by syringes using conventional plungers. In addition, the ratio of the cross-sectional area of the reservoir-disc to the injection-chamber disc appears to be less than about 8:1. As Reyman addressed the problem of delivering known, discrete quantities of fluid and was not concerned with providing high pressure fluids, the low pressure delivery characteristics of the Reyman device was not a particular concern to Reyman. In addition, Reyman's preferred embodiment uses a one-way valve between the reservoir and dispensing chamber (to prevent back flow to the reservoir during delivery) and a cap upon the opening in the dispensing chamber (to prevent loss of the fluid during inter-chamber transfer). These features make this device very complicated to operate. Lastly, Reyman does not disclose an injection chamber having a sterile inner surface.

There are a number of pneumatic injection devices disclosed in the literature as well. However, these devices often provide inadequate control of the delivery of the bone cement, and may pose safety concerns in applications such as vertebroplasty wherein control of the injected material is of paramount importance.

U.S. Pat. No. 6,033,105 ("Barker") discloses an integrated bone cement mixing and delivery system. However, Barker teaches using an auger mechanism as the means for advancing the bone cement through the delivery chamber. Barker teaches that the auger mechanism is advantageous because it provides both controlled delivery and high pressure. Barker further discloses many alternative embodiments of the device, wherein the pitch, direction and diameter of the augur threads are varied in order to maximize control, enhance delivery pressure and eliminate air bubbles in the bone cement.

The English language abstract of JP 10146559 discloses a device for injecting viscous fluids in discrete quantities which requires a reciprocating holding member (3). The English language abstract of JP 10146559 does not disclose an injection chamber having a sterile inner surface, nor does fluid communication ever exist between the reservoir and injection chamber exit openings.

U.S. Pat. No. 5,931,347 ("Haubrich") discloses a device for injecting viscous fluids in which the injection chamber has an axially movable piston which a) when moved from the entry opening of the injection chamber towards the chamber's exit opening, creates a vacuum in the chamber in order to draw fluid from reservoir into the chamber, and b) when moved in the opposite direction, has a through hole to allow the fluid to move through it to reach the exit opening of the injection chamber. Haubrich does not disclose an impermeable piston in the injection chamber.

SUMMARY OF THE PRESENT INVENTION

The present inventors have found that providing a dual chamber, mixing-and-delivery device in which the delivery chamber houses an axially movable piston provides a number of advantages over the prior art Barker device.

First, the position of the axially movable piston can be manipulated during operation to pass over and occlude the entry port of the injection chamber during a stroke. The ability to occlude the entry port allows the user to selectively stop fluid communication between the injection chamber's exit opening and the reservoir, thereby isolating the bone cement (or other injectable material) present in the injection chamber. The isolated bone cement may then be advantageously injected into the patient in small discrete quantities (such as 0.5–1 cc per stroke). This capability provides the surgeon with highly specific control of the quantity of injected cement, a quality not found in other high pressure vertebroplasty injection devices.

Second, the axially movable piston can be made to sealingly fit within a small (e.g., 1 cc) tubular injection chamber so as to force the discrete quantity of bone cement in the injection chamber in a predetermined direction under high pressure. Accordingly, a mixing-and-delivery device having both high-pressure delivery capability and a compact size is now possible.

Lastly, the axially movable piston may be attached to a lever to increase the mechanical advantage of the force used to axially move the piston, thereby further increasing the pressure within the injection chamber.

For these reasons, the device of the present invention can deliver discrete quantities of bone cement at pressures suitable for vertebroplasty (preferably, at least 1000 psi (~6.89 MPa), more preferably, at least 2000 psi (~13.8 MPa)) while maintaining overall device dimensions which are desirable for vertebroplastic surgeries. Accordingly, the device of the present invention provides significant technical advances over the conventional mixing/injection devices used in the bone cement procedures.

Therefore, in accordance with a first embodiment of the present invention, there is provided an injection device for injecting bone cement, comprising:
a) a reservoir having an exit opening,
b) an injection chamber having:
  i) first and second end portions, and
  ii) a sterile inner surface forming an entry opening in the first end portion and an exit opening in the second end portion,
the exit opening of the reservoir and the entry opening of the sterile inner surface of the injection chamber being in fluid communication therebetween, and
c) an impermeable first piston disposed within the inner surface of the injection chamber.

In accordance with a second embodiment of the present invention, there is provided a device for injecting bone cement, comprising:
a) a reservoir having an exit opening and an inner surface,
b) an injection chamber having:
  i) first and second end portions, and
  ii) a sterile inner surface forming an entry opening in the first end portion and an exit opening in the second end portion,
the exit opening of the reservoir and the entry opening of the sterile inner surface of the injection chamber being in fluid communication therebetween, and
wherein the reservoir inner surface and the injection chamber inner surface define a volume ratio of at least 10:1.

In accordance with a third embodiment of the present invention, there is provided a device for injecting bone cement, comprising:
a) a reservoir having an exit opening,
b) an injection chamber having:
  i) first and second end portions, and
  ii) a sterile inner surface forming an entry opening in the first end portion and an exit opening in the second end portion,
the exit opening of the reservoir and the entry opening of the sterile inner surface of the injection chamber being in fluid communication therebetween, and
wherein the injection chamber inner surface defines a volume of between 0.1 and 5 cc.

In accordance with a fourth embodiment of the present invention, there is provided a device comprising:
a) a reservoir having an exit opening,
b) an injection chamber having:
  i) first and second end portions and
  ii) a sterile inner surface forming an entry opening disposed at the first end portion and an exit opening disposed at the second end portion,
the exit opening of the reservoir and the entry opening of the sterile inner surface of the injection chamber being in fluid communication therebetween, and
c) a radially movable mixing element housed within the reservoir.

In accordance with a fifth embodiment of the present invention, there is provided a device comprising:
a) a reservoir having an exit opening,
b) an injection chamber having:
  i) first and second end portions and
  ii) a sterile inner surface forming an entry opening disposed at the first end portion and an exit opening disposed at the second end portion,
the exit opening of the reservoir and the entry opening of the sterile inner surface of the injection chamber being in fluid communication therebetween, and
c) means for preventing back flow from the exit opening of the injection chamber.

In accordance with a sixth embodiment of the present invention, there is provided a device for injecting bone cement, comprising:
a) a reservoir having an exit opening,
b) an injection chamber having:
  i) first and second end portions and
  ii) a sterile inner surface forming an entry opening disposed at the first end portion and an exit opening disposed at the second end portion,
the exit opening of the reservoir and the entry opening of the sterile inner surface of the injection chamber being in fluid communication therebetween, and
c) means for manually ejecting bone cement in discrete quantities from the injection chamber under a pressure of at least 1000 psi (6.89 MPa).

In accordance with a seventh embodiment of the present invention, there is provided a device for injecting bone cement comprising:

a) a reservoir having first end portion forming an exit opening and a second end portion,
b) an injection chamber having:
   i) first and second end portions and
   ii) a sterile inner surface forming an entry opening disposed at the first end portion and an exit opening disposed at the second end portion,
the exit opening of the reservoir and the entry opening of the sterile inner surface of the injection chamber being in fluid communication therebetween, and
c) means for applying continuous pressure upon bone cement located in the reservoir.

In accordance with a eighth embodiment of the present invention, there is provided an injection device for injecting bone cement, comprising:
a) a reservoir having an exit opening,
b) an injection chamber having:
   i) first and second end portions, and
   ii) a sterile inner surface forming an entry opening disposed at the first end portion and an exit opening disposed at the second end portion,
the exit opening of the reservoir and the entry opening of the sterile inner surface of the injection chamber being in fluid communication therebetween,
c) mechanical advantage means for pressurizing the injection chamber.

In accordance with a ninth embodiment of the present invention, there is provided an injection device for injecting bone cement, comprising:
a) a reservoir having an exit opening,
b) an injection chamber having:
   i) first and second end portions, and
   ii) a sterile inner surface forming an entry opening disposed at the first end portion and an exit opening disposed at the second end portion,
the exit opening of the reservoir and the entry opening of the sterile inner surface of the injection chamber being in fluid communication therebetween,
c) a shaft having a first end portion and a second end portion, wherein the second end portion of the inner surface has a third opening and the second end portion of the shaft is slidably received in the third opening.
d) a lever having first and second end portions, the first end of the lever being connected to the device, the second end of the lever positioned to bear upon the second end portion of the shaft, wherein at least one end portion of the lever is pivotally connected.

In accordance with a tenth embodiment of the present invention, there is provided an injection device for injecting bone cement, comprising:
a) a reservoir having an exit opening,
b) an injection chamber having:
   i) first and second end portions, and
   ii) a sterile inner surface forming an entry opening disposed at the first end portion and an exit opening disposed at the second end portion,
the exit opening of the reservoir and the entry opening of the sterile inner surface of the injection chamber being in fluid communication therebetween,
c) means for creating a vacuum in the injection chamber between the entry and exit openings.

In accordance with a eleventh embodiment of the present invention, there is provided a device comprising:

a) a reservoir having an exit opening,
b) an injection chamber having:
   i) first and second end portions and
   ii) a sterile inner surface forming an entry opening disposed at the first end portion and an exit opening disposed at the second end portion,
the exit opening of the reservoir and the entry opening of the sterile inner surface of the injection chamber being in fluid communication therebetween, and
c) an O-ring contacting the inner surface of the injection chamber.

In accordance with a twelfth embodiment of the present invention, there is provided an injection device for injecting bone cement, comprising:
a) a reservoir having an exit opening,
b) an injection chamber having i) a sterile inner surface forming entry and exit openings, and ii) first and second ends defining a first axis, the exit opening of the reservoir and the entry opening of the sterile inner surface of the injection chamber being in fluid communication therebetween,
c) a first piston disposed within the inner surface of the injection chamber and having a first piston having an inner face facing the exit opening of the injection chamber,
d) a second piston disposed within the reservoir and having an inner face facing the exit opening of the reservoir, and
wherein the inner faces of the first and second piston define respective first and second cross-sectional areas, and wherein the ratio of the second cross-sectional area to the first cross-sectional area is at least 9:1.

DESCRIPTION OF THE FIGURES

FIGS. 6a–c present cross-sectional views of preferred features within the reservoir of the present invention.

DETAILED DESCRIPTION OF THE INVENTION

For the purposes of the present invention, "sterile" means a sterility assurance level of no more than $10^{-6}$. An "axially movable" piston includes the leading face of both a plunger and the leading face of a screw which is threadably engaged with a correspondingly threaded tube. When one component "bears against" another component, it may do so indirectly. Likewise, when two components are "connected", they need not have direct physical contact. When two components "contact" each other, they directly touch each other. When two components "engage" or "attach to" each other, they fit together.

Figure 1:
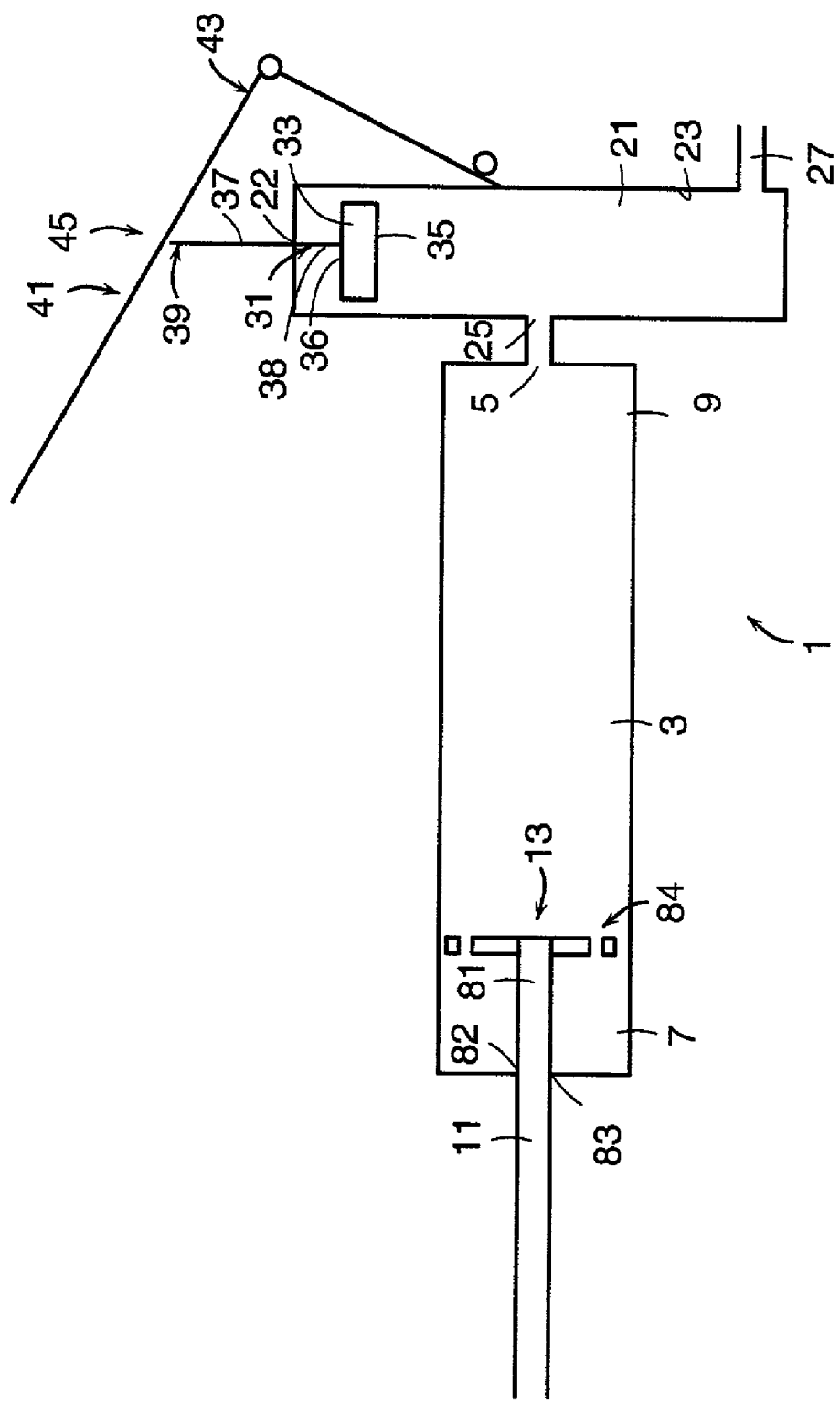
FIG. 1 presents a cross-sectional view of an embodiment of the device of the present invention.

Now referring to FIG. 1, there is provided a preferred embodiment of the present invention, wherein the device 1 for mixing and injecting bone cement, comprises:
a) a reservoir 3 having an exit opening 5 and first and second ends (7,9) defining a reservoir axis,
b) a first member 11 having a mixing shank 13 extending therefrom, the shank being disposed within the reservoir,
c) an injection chamber 21 comprising i) a sterile tubular inner surface 23 forming entry and exit openings (25,27), the exit opening 5 of the reservoir and the entry opening 25 of the sterile inner surface of the injection chamber being in fluid communication therebetween,
d) a plunger 31 slidably received in an opening 22 in the tubular inner surface 23 of the chamber, the plunger comprising i) a piston 33 having an inner face 35 and an outer face 36, and ii) a plunger rod 37 having first and second ends (38,39), the inner face 35 of the piston facing the exit opening 27 of the injection chamber and being in sealing engagement with the inner surface 23 of the injection chamber, the outer face 36 of the piston being attached to the first end 38 of the second rod, and
e) a lever 41 having first and second ends (43,45), the first end 43 of the lever being pivotally attached to the device 1, the second end 45 of the lever being attached to the second end 39 of the plunger rod.

Figure 2A:
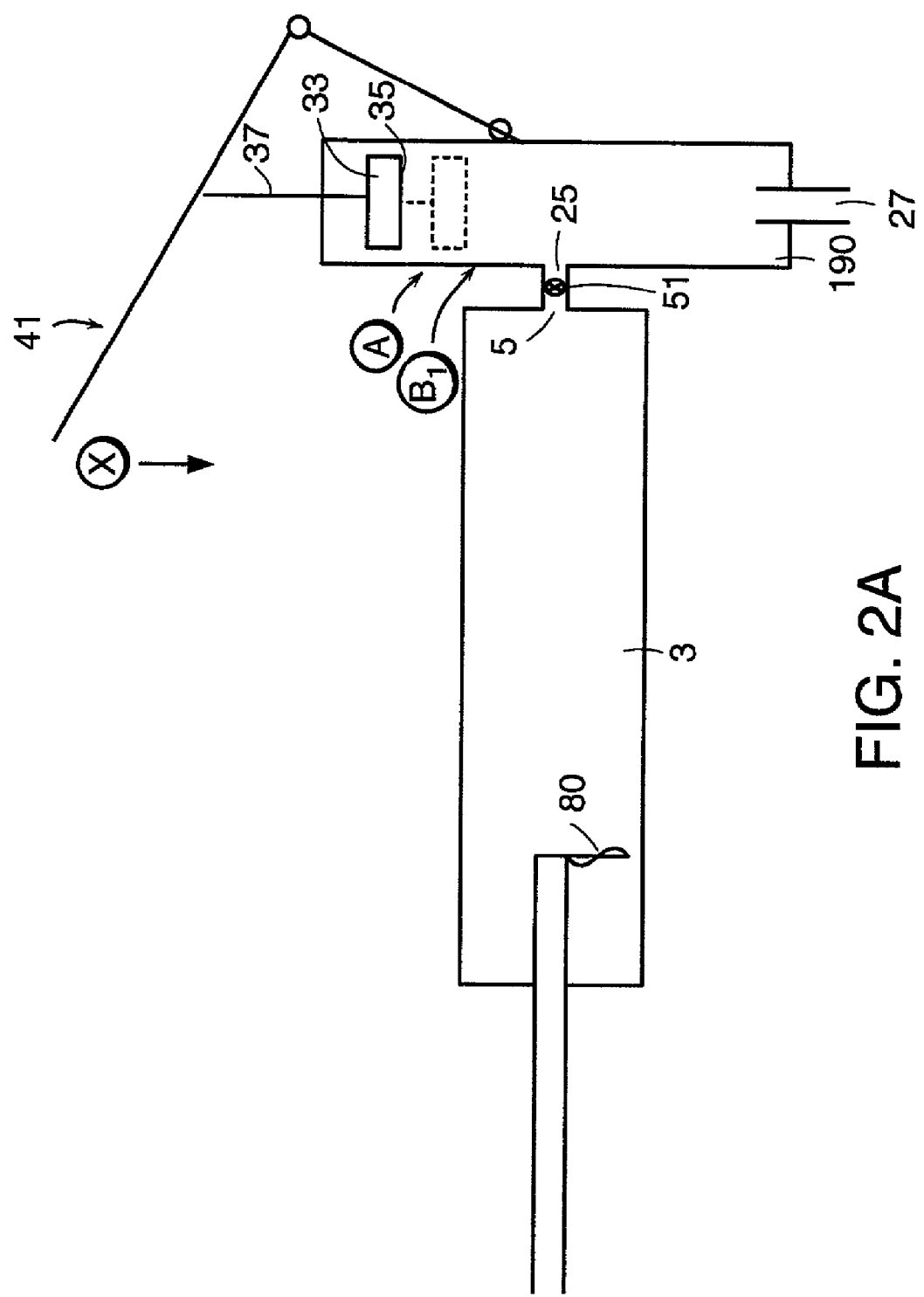
FIGS. 2a–c present cross-sectional views of preferred injection chambers in devices of the present invention having a plunger.

Now Referring to FIG. 2a, in some embodiments, when a force X is applied to lever 41 in a direction parallel to plunger rod 37, the forward action of piston 33 begins at position A and ends at position $B_1$, thereby displacing an amount of bone cement equal to the traversed volume through exit opening 27. However, since the piston of this embodiment does not pass over the entry opening of the injection chamber, at no time in the stroke does this piston prevent fluid communication between the reservoir and injection chamber, and so the pressure is determined by the pressure of the fluid in reservoir 3 (which is typically low). Therefore, in some embodiments, a valve 51 is provided between the entry opening 25 of the sterile inner surface of the injection chamber and the exit opening 5 of the reservoir for restricting the fluid communication therebetween. When this valve 51 is in an open position, bone cement may be delivered from the reservoir into the injection chamber. After such delivery, valve 51 is adjusted to its closed position, and the bone cement in the injection chamber is now in fluid isolation. Accordingly, the pressure experienced by the cement is now a function of the diameter of the inner face 35 of piston 33 of the injection chamber, and so the isolated cement may be more easily pressurized to a usefully high pressure by the forward action of the lever 41.

Although valve 51 is useful in enhancing the pressure of the bone cement in the injection chamber, it nonetheless requires extra effort to open and shut the valve with each stroke. Now referring to FIG. 2b, in more preferred embodiments, the stroke of the plunger is such that piston 33 of the plunger begins its stroke at position A (thereby allowing fluid communication between the entry 25 and exit 27 openings), and then moves forward across the entry opening 25 during the injection stroke to position $B_2$, thereby occluding the entry opening and preventing the fluid communication with the reservoir. Since the bone cement in the injection chamber is now in fluid isolation, the pressure experienced by the cement is now a function of the diameter of the inner face 35 of the injection chamber piston 33 and so may be more easily pressurized to a usefully high pressure by the forward action of the lever 41.

In this preferred embodiment, the dual role played by the piston 33 obviates the need for the valve member 51.

Figure 2C:
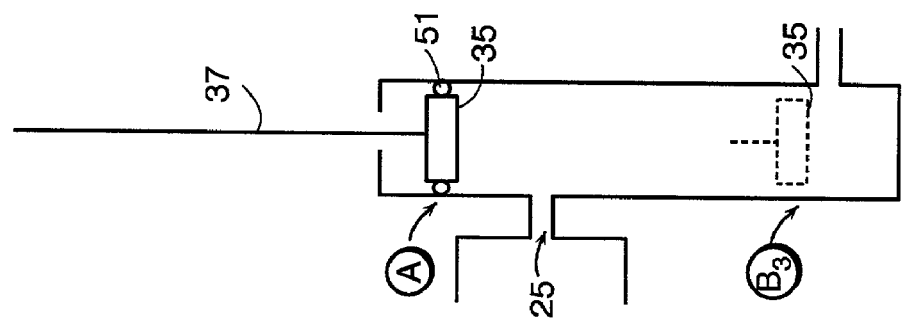
Figure 2B:
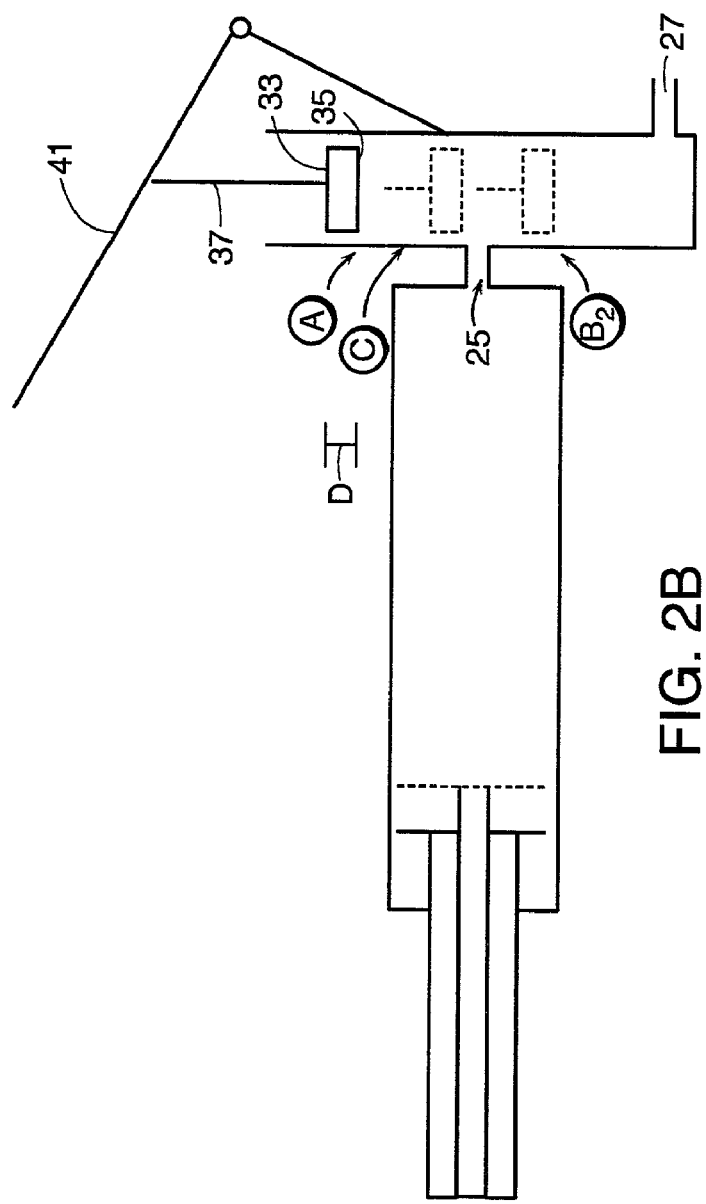

Although the device of FIG. 2b provides the isolation desired for discrete bone cement injection, it does so for only a relatively small portion of the stroke. That is, when the inner face is between positions A and C, fluid communication still exists between the reservoir and injection chambers, and so only relatively low pressures can be realized. Therefore, in more preferred embodiments, the length of plunger 37 is such that the inner face 35 of the piston has an initial position C adjacent the entry opening 25 of the injection chamber. When the inner face is so positioned, the only portion of the stroke in which fluid communication still exists is that small portion in which inner face 35 passes over entry opening 25. Therefore, this embodiment has the advantage that virtually the entire stroke is at a high pressure. Preferably, the depth D of piston 33 is greater than the distance between entry opening 25 and exit opening 27. This condition prevents cement from flowing from the reservoir into the area of the injection chamber behind the piston.

In one preferred embodiment, now referring to FIG. 2c, the length of plunger rod 37 is such that the inner face 35 of the piston has a final position $B_3$ substantially adjacent the exit opening 27 of the injection chamber. In this mode, the plunger movement completely empties the chamber of bone cement. This has the advantage of providing more ejection volume per stroke, thereby requiring fewer strokes to deliver a predetermined volume.

Preferably, the inner face of the piston housed within the injection chamber is sealingly engaged with a smooth inner surface of a tubular injection chamber. Under such sealing engagement conditions, the forward action of the inner face upon the isolated bone cement can produce the desired high pressure. However, in other embodiments and now referring to FIG. 3, the axially movable inner face 34 may be the lead surface of a screw 60 having a thread 61 which is threadably engaged with a corresponding thread 62 of the tubular injection chamber 21, thereby providing a sealing engagement. Since the inner face is axially movable relative to the injection chamber and the sealing engagement allows the bone cement to be isolated, the bone cement within the injection chamber may be easily pressurized to a high pressure. By way of contrast, the auger design of Barker discloses a threaded screw within a smooth tube and so does not produce the total occlusion condition desired for producing high pressures.

In preferred embodiments, the inner face 34 or 35 of the piston is impervious to viscous bone cement. The impervious nature of the inner face allows the movement of the inner face to efficiently act upon the bone cement within the injection chamber and thereby produce a high pressure. By way of contrast, the auger of Barker requires that bone cement pass through the inner face in order to be injected.

In some embodiments, referring again to FIG. 3, the device further comprises a check valve 65 located adjacent the exit opening 27 of the injection chamber. During the low pressure filling of the injection chamber, this valve is in a closed position (position C) which seals the exit opening from fluid flow. During the high pressure stroke, check valve 65 opens (position D) in response to increased pressure within the injection chamber and then recloses (position C) upon reduction of that pressure below a predetermined high pressure level. This feature prevents bone cement from being sucked back into the injection chamber from the delivery tube (not shown) during the low pressure refilling of the injection chamber.

Figure 3:
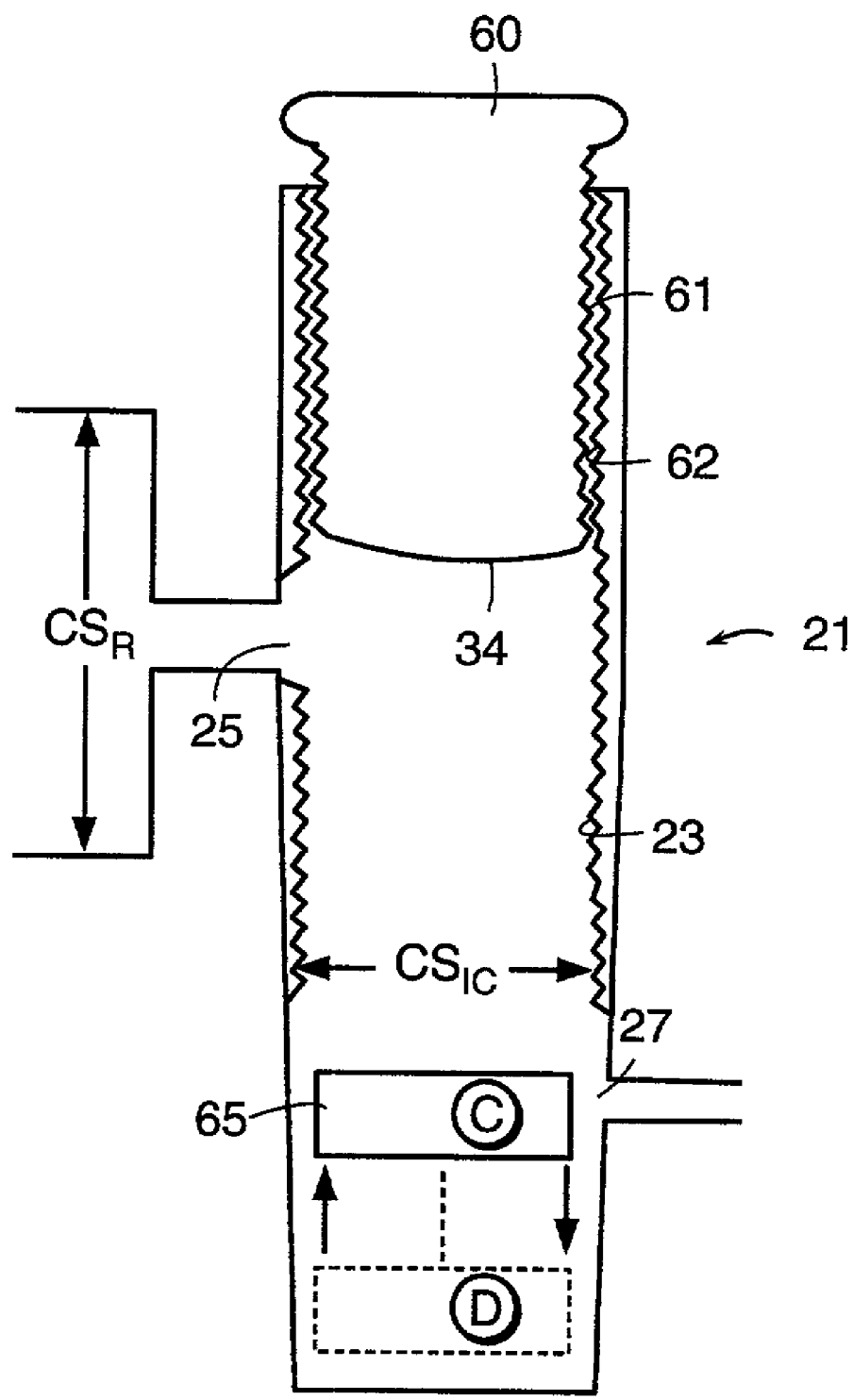
FIG. 3 presents a cross-sectional view of a preferred injection chamber in a device of the present invention having a screw.

Although check valve 65 of FIG. 3 successfully prevents cement back flow during the evacuation of the injection chamber, it nonetheless requires the injection chamber to have an angled portion. When very viscous cement is used, it is more desirable to have a substantially linear flow line in the injection chamber. Therefore, in some embodiments, and now referring to FIGS. 11a and 11b, check valve 65 is replaced with a flow restrictor and the flow path in the injection chamber is substantially in-line. For the purposes of the present invention, the "flow path" is defined as the straight line connecting the center of the inner face of the piston with the center of the exit opening. The intersection of this flow path with a line orthogonal to the inner face of the piston defines an angle. When this angle is less than 45 degree, the flow path is substantially in-line. Preferably, the angle is less than 30 degrees.

Figure 11A:
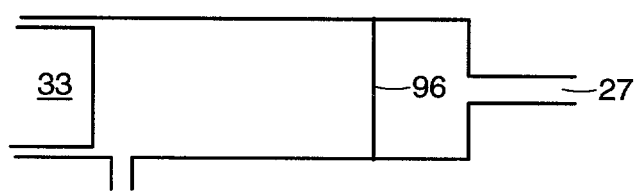
FIGS. 11a–b disclose preferred embodiments of the device having a fluid flow restrictor.
Figure 11B:
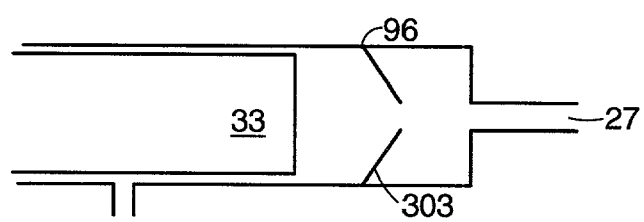
Figure 11C:
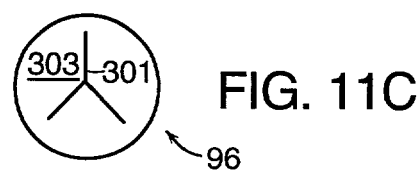
FIG. 11c discloses an axial view of a preferred flow restrictor.

The flow restrictor 96, as shown in FIGS. 11a–b, is a thin disc disposed normal to and within the injection chamber tube configured to generally restrict flow therethrough under low pressure but allow flow therethrough under higher pressure. This disc preferably has a plurality of slits 301 which create flaps 303. When the piston moves towards the flow restrictor, the high pressure in the injection chamber forces the flaps open, thereby permitting flow. When the piston is retracted, the flaps recede to their original position, thereby preventing back flow. Preferably, the disc is made of a flexible material such as polyethylene and comprises at least 2 slits, more preferably at least three slits, as shown in FIG. 11c.

Figure 10:
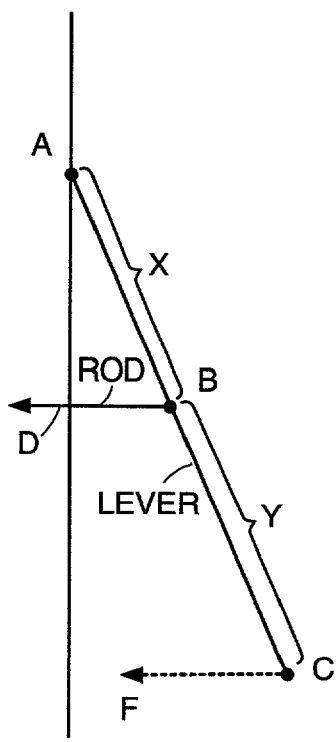
FIG. 10 describes the concept of mechanical advantage provided by levers.

In some embodiments using a lever arm to axially move the injection chamber piston, the pressure generatable by forward action of the lever is a function of the mechanical advantage of the lever. Now referring to FIG. 10, there is provided a lever L pivotally attached to plane P at point A. Also, Rod R is engaged with lever L at point B and is slidably received in Plane P at point D. The mechanical advantage gained by pushing rod R with lever L with a force F at point C is calculated as $$MA = \frac{x+y}{x}.$$

wherein the distance AB along the lever is X, and the distance BC along the lever is Y. Generally, the lever arm is attached to the plunger rod at an attachment point which provides a mechanical advantage of more than 1. Preferably, the mechanical advantage is at least 2, more preferably at least 3, most preferably at least 5.

As noted above, the pressure experienced by a fluid in a tube in response to the forward action of a plunger is inversely related to the cross sectional area (CS) of the inner face of the plunger. Accordingly, an inner face having a small cross sectional area is capable of producing a higher pressure than an inner face having a much higher cross section. Therefore, again referring to FIG. 3, a highly desirable feature of the injection chamber is its reduced cross-section $CS_{ic}$ relative to that of the reservoir $CS_r$, which allows the bone cement to be more easily pressurized to a high pressure. Preferably, the ratio of the cross-sectional area of the reservoir $CS_r$ to the cross-sectional area of the injection chamber $CS_{ic}$ is at least 9:1. More preferably, it is at least 15:1. When the more preferred ratio is adopted, a device having a relatively short reservoir and yet a surgically useful injection chamber may be realized. In one embodiment, the reservoir holds 30–40 cc of bone cement and has a 5–6 inch length (~127–154 mm), and the injection chamber contains 0.5–1 cc of bone cement, and the $CS_r$:$CS_{ic}$ ratio is about 10.3:1.

As shown in FIG. 1, the bone cement precursors are mixed by a porous disc 13 attached to the end of first member 11. Preferably, first member 11 is a rod comprising a first end 81 (to which disc 13 is attached) and a second end 82 which is slidably received in the reservoir via an opening 83 in the second end 7 of the reservoir. This disc has transverse holes 84 which allow for passage and agitation of the bone cement precursors when the mixing rod is moved axially about the reservoir, thereby insuring the complete mixing of these precursors. In some embodiments, the disc has a diameter which is substantially less than the diameter of the reservoir, thereby enhancing its ability to agitate the bone cement precursors. In other embodiments, the mixing shank comprises a blade 80 as in FIG. 2, which agitates the bone cement precursors when the mixing rod is rotated about the reservoir axis.

The bone cement may be delivered from the reservoir to the injection chamber by providing a pressure differential. For example, the pressure differential may be produced by gravity by simply positioning the reservoir at a higher elevation. In some embodiments, the bone cement is delivered from the reservoir to the injection chamber by pressurizing the bone cement in the reservoir via a pressurizing means. In one preferred embodiment and now referring to FIG. 4, there is provided a second piston 71 housed within the reservoir 3 and having an inner face 72 facing the exit opening 5 of the reservoir. When this inner face 72 moves axially toward the exit opening 5 of the reservoir, it pushes the bone cement in that direction, thereby forcing the bone cement into the injection chamber. Preferably, the inner surface 78 of the reservoir has a tubular shape, and the inner face 72 of the second piston 71 is in sealing engagement with the inner surface 78 of the reservoir. Preferably, the inner surface 78 of the tubular reservoir is smooth and the second piston 72 is slidably received within the tubular shape.

Figure 4:
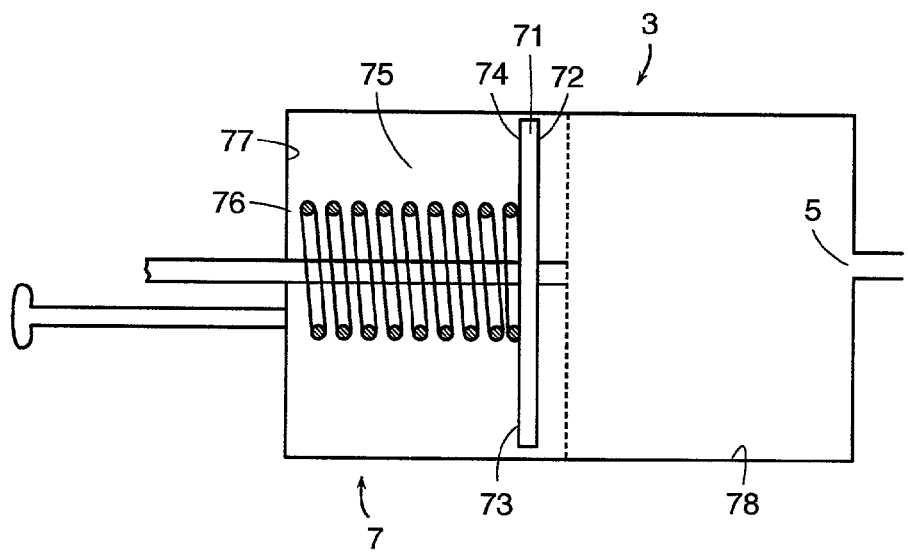
FIG. 4 presents a cross-sectional view of a reservoir of the present invention.
Figure 7:
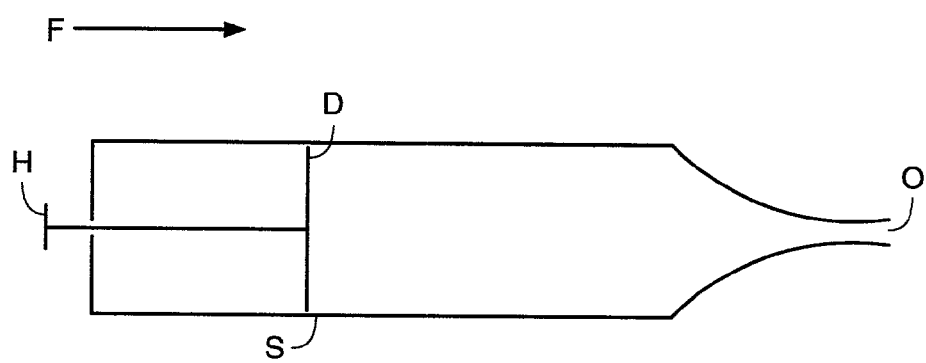
FIG. 7 presents a cross-sectional view of a conventional syringe having a conventional plunger.

More preferably, now referring to FIG. 4, there is provided a spring-loaded plunger comprising a spring 75 having a first end 74 contacts the outer face 73 of the second piston 71 and a second end 76 contacts the back surface 77 of the reservoir. In this embodiment, the spring-loaded plunger exerts a substantially continuous pressure upon the bone cement in the reservoir as the piston advances towards the exit opening, thereby forcing the cement into the injection chamber when the injection chamber is empty and inner face 35 of the plunger is pulled back to position A to provide fluid communication between the injection chamber and reservoir (as shown in FIG. 2a). This automatic re-filling feature of the device eases operation of the device.

Figure 9A:
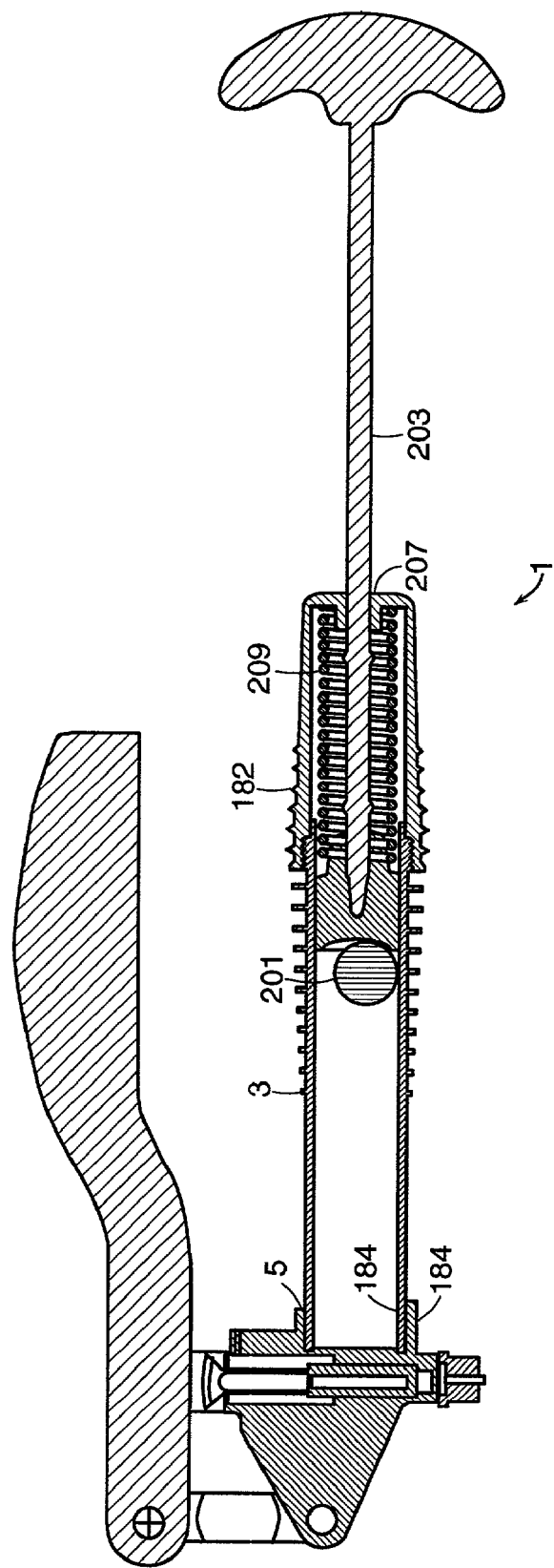
FIGS. 9a–b present preferred embodiments of the present invention having a freely movable mixing element in the reservoir.
Figure 9B:
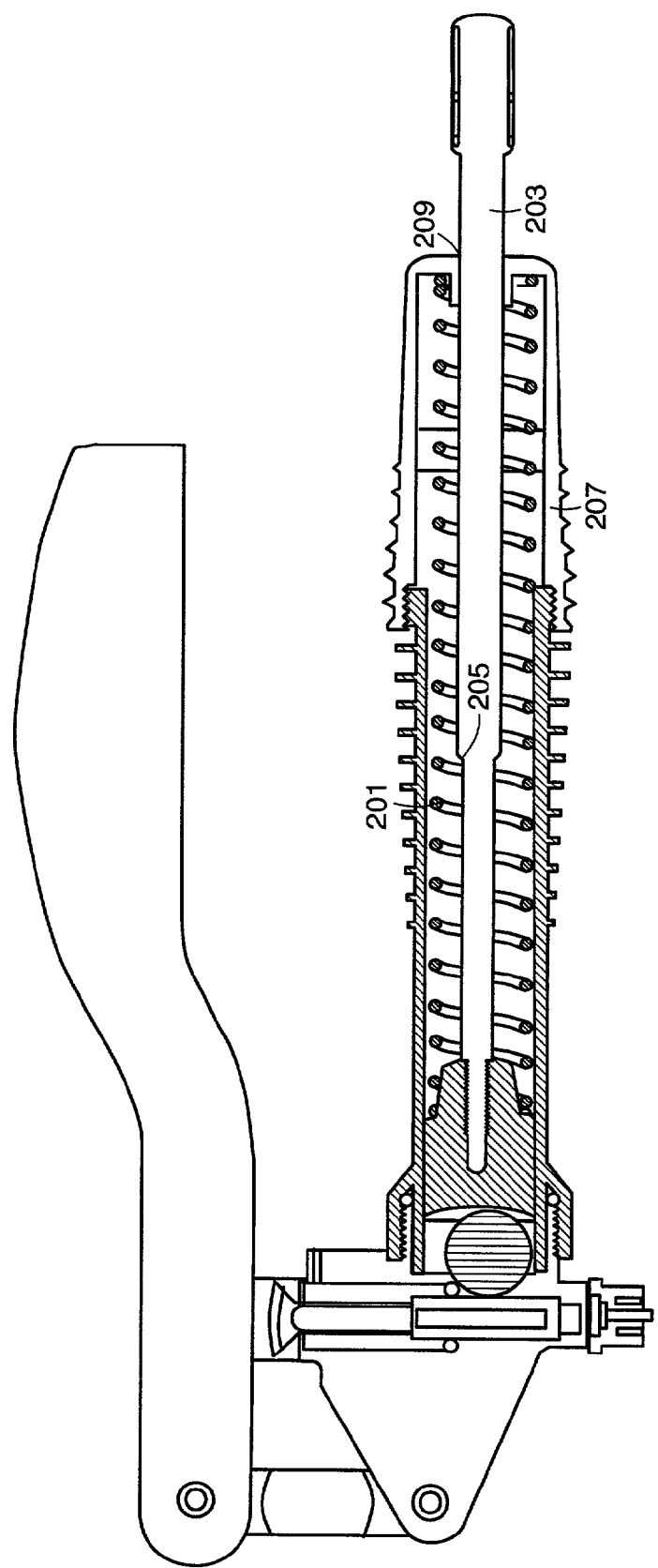
Figures 9C, 9D:
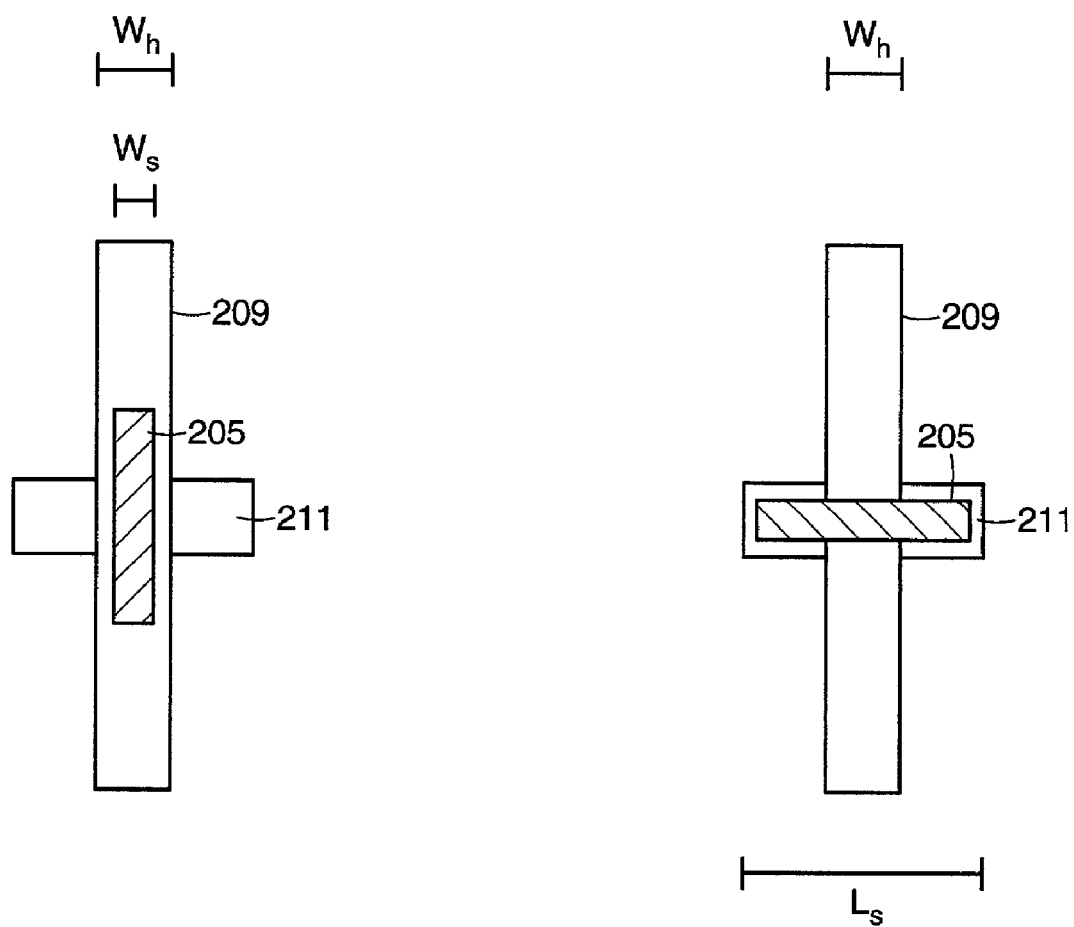
FIGS. 9c–d present axial views of respective unlocked and locked embodiments of the spring-loaded embodiments of the invention.

In some embodiments, the spring may be loaded and locked into place. Now referring to FIG. 9b (which discloses a device of the present invention in which the spring is in its relaxed position), to load the spring 201, spring rod 203 having shoulder 205 is manually retracted so that the shoulder 205 exits the reservoir 207 through hole 209, the hole 209 having a shape accommodating the shoulder 205 cross section. Now referring to FIG. 9c, the width $W_h$ of hole 209 is such that it allows passage of narrow rod portion 213 and the width $W_s$ of shoulder 205 , but not the length $L_s$ of shoulder 205. Now referring to FIG. 9d, once shoulder 205 is outside the hole 209, rod 203 may be rotated 90 degrees and then released so that, as the spring 201 pulls the rod 203 back into the reservoir 207, shoulder 205 bears against grooves 211 disposed about hole 209, thereby locking the rod 203 into place. The spring-loaded device of the present invention is shown in FIG. 9a.

Figure 5:
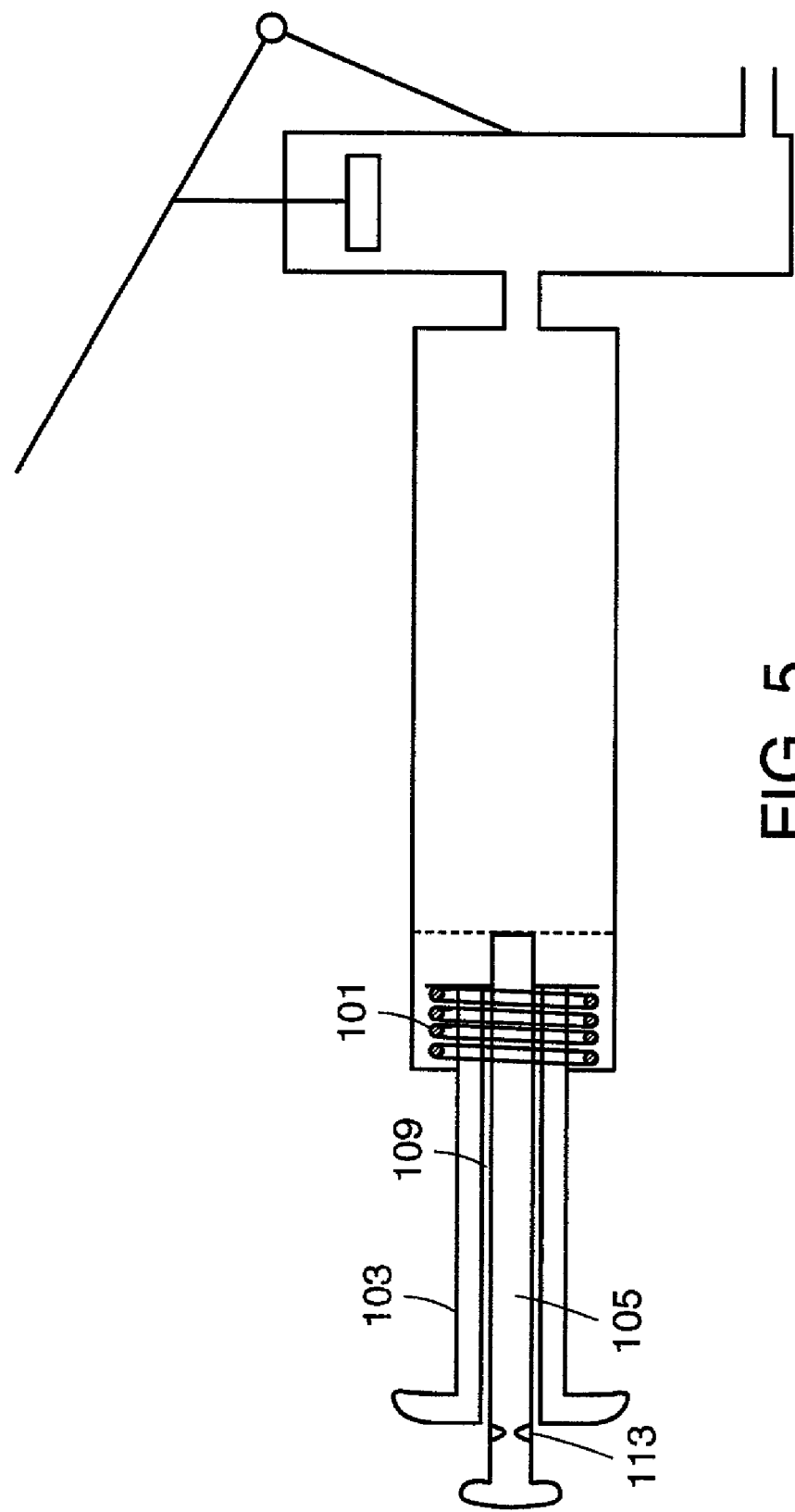
FIG. 5 presents a cross-sectional view of an embodiment of the present invention having a mixing handle and a spring loading handle.

In some embodiments, as in FIG. 5, spring 101 is both retracted and released via handled spring rod 103. When this embodiment is adopted, it is preferred that the second end 105 of the mixing rod be slidably received within a bore 109 axially located within the handled spring rod 103. This feature has the advantages of economizing reservoir space and ensuring that both the porous disc and the plunger piston act throughout the entire cross section of the reservoir. In one preferred mode of operation, once the mixing step is completed, the mixing handle is broken off at a thinned break point 113 near the second end 105 of handled spring rod 103.

As noted above, the two-handle embodiment of FIG. 5 is a complex device. Accordingly, in some embodiments, the handle for locking the spring is eliminated and replaced with a locking pin. Now referring to FIG. 6a, there is provided a pair of locking pins 85 for maintaining spring 75 in a compressed or loaded position. Reservoir wall 87 further possesses a pair of holes 86a, 86b for receiving the locking pins 85. Preferably, and now referring to FIG. 6b, second piston 71 also possesses a pair of recesses 88 about its periphery shaped for receiving the pins. During fabrication, the pins sequentially enter first the reservoir recesses 86 and then the piston recesses 88 to lock the pre-loaded spring in place. In use, the pins remain in place while the cement precursors are adequately mixed. Once the mixing is completed, the pins 85 are removed, thereby freeing pre-loaded spring 75 to force the inner face 72 of piston 71 to press against the cement, thereby pressurizing the cement for delivery into the injection chamber. In some embodiments, and now referring to FIG. 6c, locking tynes 89 are connected by a shaft 90 to form a single locking pin 85.

The materials of the present invention can be any suitable biomaterial, such as metals or plastics. Because the device is used to deliver sterile bone cement, the materials should also be sterile. In some embodiments, the inner surface of the reservoir wall 87 is also sterile. Preferably, all the surfaces which contact the bone cement are sterile. Since bone cements are also known to degrade and/or affect many materials, these surfaces should also be compatible with the bone cement.

EXAMPLE I

Figure 8A:
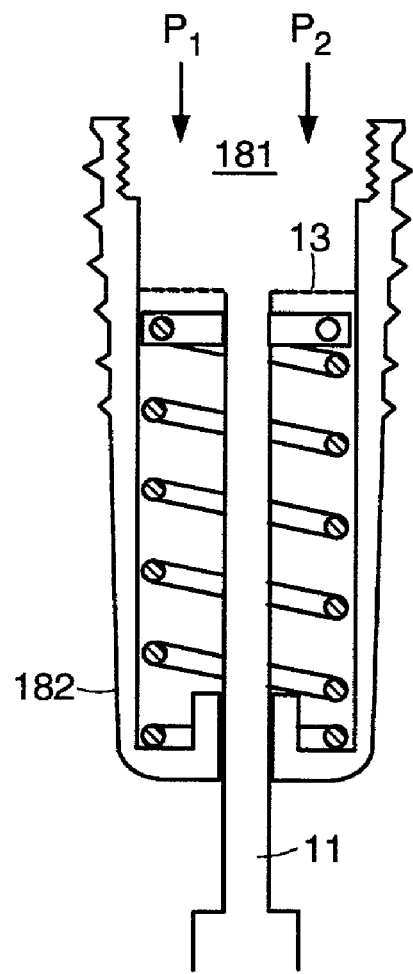
FIGS. 8a–b present cross-sectional views of preferred features within the reservoir of the present invention.
Figure 8B:
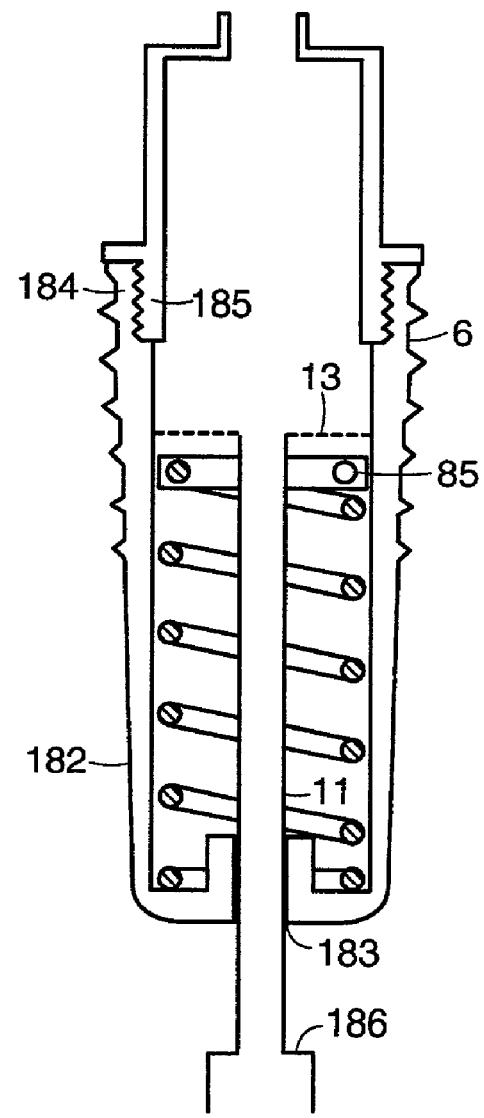

Now referring to FIGS. 8a and 8b, the PMMA precursors $P_1$ and $P_2$ are first poured into the opening 181 at the first end 6 of the reservoir cap 182. Threaded reservoir cap 182 having a threaded end 184 and a hole 183 for slidably receiving mixer rod 11 is then screwed onto the corresponding thread 185 of the reservoir 3 to produce the device as shown in FIG. 8b. Next, the mixing rod 11 is unlocked by rotating rod 11 so that shoulder 186 passes through hole 183, and the mixing rod 11 is axially cycled along the first axis of the reservoir, thereby causing the mixing disc 13 to move axially within the reservoir. The axial movement of the porous mixing disc causes agitation of the precursors, which react on contact to produce a well-mixed cement.

When mixing is completed and the bone cement is well-mixed, locking pins 85 are removed, thereby releasing compacted spring 75 and pressurizing the cement.

Now referring to FIGS. 2a–c and 3, in order to deliver the bone cement to the injection chamber, the second end of lever 41 is pulled back away from the injection chamber. As the lever is so retracted, piston 35 of plunger 37 is retracted away from the entry opening of the injection chamber, thereby providing fluid communication between the reservoir and the injection chamber. Bone cement under pressure by the spring-loaded plunger is forced through the exit opening 5 of the reservoir, through entry opening 25 of the injection chamber and into injection chamber 21. Because the relatively low pressure provided by the spring loaded plunger is below that required to open check valve 65, optional check valve 65 remains in a closed state, thereby preventing low pressure ejection of any bone cement through exit opening 27.

To deliver cement through exit opening 27, lever 41 is urged toward the injection chamber 21 from position C to position $B_1$. When this occurs, the inner face 35 of piston 33 moves over and occludes entry opening 25 and moves towards exit opening 27. This movement of the inner face 33 pressurizes the bone cement housed in the injection chamber to a pressure exceeding the critical pressure of the closed check valve. As a result, normally closed check valve 65 now opens and bone cement is forced through exit opening 27 and is injected into the patient via a tube (not shown).

Alternatively, check valve 65 is replaced with flow restrictor 96 (as shown in FIG. 11a), and exit opening 27 is located at the position on the far wall 190 of the injection chamber (as shown in FIG. 2a) so that the bone cement exits the chamber in a direction parallel to the axis of the tubular injection chamber. In use, the high presure caused by the advance of piston 33 forces open flaps 95, thereby allowing substantially in-line flow of cement from the piston to exit opening 27.

In accordance with the first embodiment, it is preferred that the the first and second end portions of the injection chamber define a first axis within the inner surface, wherein the first piston comprises a sidewall having a shape corresponding to the inner surface of the injection chamber, and the first piston is received within the inner surface to allow axial movement of the first piston along the first axis within the inner surface. The piston correspondence with inner surface shape allows easy axial movement of the piston.

It is preferred that the first piston is slidably received within the inner surface to allow sliding movement of the first piston along the first axis within the inner surface.

It is preferred that the shape of the first piston sidewall provides substantial sealing engagement with the inner surface. This conditions prevents the flow of bone cement therebetween.

It is preferred that the first piston has an inner face facing the exit opening of the injection chamber, the inner face has a centerpoint, and the centerpoint and exit opening of the injection chamber define a flowpath which is substantially linear. This is desirable for viscous bone cements. More preferably, the flow path has an angle of less than 30 degrees.

Now referring to FIG. 2c, it is preferred that the device further comprising an O-ring 51 disposed between the sidewall of the first piston and the inner surface of the injection chamber. The O-ring prevents air bleed in.

It is preferred that inner surface of the injection chamber has a tubular shape corresponding to the first axis, the sidewall has a threaded surface, and the tubular inner surface is correspondingly threaded for receiving the threaded sidewall to allow axial movement of the inner face of the first piston along the inner surface. This describes a screw which can provide mechanical advantage.

It is preferred that the first piston has an inner face facing the exit opening of the injection chamber, and the inner face is movable within the inner surface from a first position in the first end portion of the injection chamber to a second position in the second end portion of the injection chamber, wherein the first position of the first piston allows for fluid communication between the entry and exit openings of the sterile inner surface of the injection chamber, and wherein the second position of the first piston restricts fluid communication between the entry and exit openings of the sterile inner surface of the injection chamber. In this embodiment, the piston acts as a valve to provides discrete quantities.

It is preferred that the first and second positions define a maximum distance over which the first piston is movable along the first axis, and wherein the movement of the inner face from the first position to the second position defines an inner surface volume of between 0.1 cc and 5 cc. This provides discrete quantities of the volumes desired in vertebroplasty. Preferably, the volume is between 0.5 cc and 2 cc.

It is preferred that the entry opening has a diameter, and the first piston sidewall has a length greater than the diameter of the entry opening. This long sidewall can fully occlude the entry opening of the injection chamber).

It is preferred that the exit openings are in fluid communication when the inner face of the first piston is located in the first end portion.

It is preferred that the sidewall of the first piston and the inner surface are in sealing connection, and the inner face of the first piston is movable from the second position to the first position. This sealing creates a vacuum upon pullback which allows auto-refill.

It is preferred that the second position of the first piston inner face is substantially adjacent to the exit opening. This allows near-complete emptying of chamber.

It is preferred that the device further comprises means for axially moving the first piston with mechanical advantage.

It is preferred that such means is a shaft having a first end portion and a second end portion, wherein the first piston further comprises an outer face, the second end portion of the inner surface has a third opening, the outer face of the piston is connected to the first end portion of the shaft, and the second end portion of the shaft is slidably received in the third opening.

It is preferred that the device further comprises a lever having first and second ends, the first end of the lever being connected to the device, the second end of the lever positioned to bear upon the second end of the shaft, wherein at least one end portion of the lever is pivotally connected.

In some embodiments, the device further comprises a lever having first and second ends, the first end of the lever being pivotally connected to the device, the second end of the lever positioned to bear upon the second end of the shaft.

In some embodiments, the second end of the lever contacts the second end of the shaft. Preferably, the second end of the lever is connected to the second end of the shaft. More preferably, the second end of the lever is attached to the second end of the shaft. More preferably, the second end of the lever is pivotally attached to the second end of the shaft.

In some embodiments, the device further comprises an arm having a first end attached to the device and a second end attached to the first end of the lever, wherein at least one end of the arm is pivotally attached.

It is preferred that the device further comprises a lever having first and second ends, the first end of the lever positioned to bear upon the device, the second end of the lever being pivotally connected to the second end of the shaft.

In some embodiments, the first end of the lever contacts the device. Preferably, the first end of the lever is connected to the device. More preferably, the first end of the lever is attached to the device. More preferably, the first end of the lever is pivotally attached to the device.

It is preferred that the second end of the lever bears against the second end of the shaft at a location to produce a mechanical advantage of more than 1, preferably at least 2, more preferably at least 3, most preferably at least 5.

It is preferred that the outer face of the piston is integral with the first end portion of the shaft.

It is preferred that the device further comprises a check valve located downstream of the reservoir, the check valve being biased in a normally closed position sealing the exit opening, the check valve being automatically openable in response to increased pressure within the injection chamber and automatically recloseable upon reduction of the pressure increase below a predetermined level.

It is preferred that the device further comprises a check valve located downstream of the reservoir for sealing the exit opening, the check valve being manually openable and closeable.

It is preferred that the first piston has an inner face, and further comprising d) a flow restrictor disposed within the inner surface of the injection chamber between the inner face of the first piston and the exit opening of the injection chamber, the restrictor comprising a slitted sheet normally disposed parallel to the inner face of the first piston, wherein the slitted sheet comprises flaps formed by slits, wherein said flaps are oriented towards the exit opening of the injection chamber in response to increased pressure from the direction of the first piston, and the flaps return to a position parallel to the inner face upon reduction of the increased pressure, thereby restricting backflow.

It is preferred that the device further comprises means for restricting back flow, the means disposed within the inner surface of the injection chamber between the inner face of the first piston and the exit opening of the injection chamber.

It is preferred that the device further comprises a second piston disposed within the reservoir and having an inner face facing the exit opening of the reservoir, wherein the first piston has an inner face facing the exit opening of the injection chamber, and wherein the inner faces of the first and second pistons define respective first and second cross-sectional areas, and wherein the ratio of the second cross-sectional area to the first cross-sectional area is at least 9:1.

It is preferred that the device further comprises a valve positioned between the first opening of the sterile inner surface of the injection chamber and the exit opening of the reservoir for restricting the fluid communication therebetween.

In accordance with the second embodiment (which requires a reservoir/injection chamber volume ratio of at least 10:1), it is preferred that the reservoir inner surface and the injection chamber inner surface define a volume ratio of at least 20:1 (more preferably at least 50:1, most preferably at least 80:1).

In accordance with the third embodiment (which requires an injection chamber volume of between 0.1 and 5 cc), it is preferred that the injection chamber inner surface defines a volume of between 0.5 and 2 cc.

It is preferred that the device further comprises a shaft having a mixing shank extending therefrom, wherein the reservoir further comprises an inner surface and first and second ends defining a reservoir axis within the inner surface of the reservoir, and wherein the shaft is axially disposed within the reservoir.

It is preferred that the shank is a disc having transverse holes therethrough, the shaft has first and second ends, the disc is attached to the first end of the shaft, the second end of the reservoir has a fourth opening, and the second end of the shaft is slidably received in the fourth opening.

It is preferred that the device further comprises a second piston housed within the reservoir and having an inner face facing the exit opening of the reservoir.

Preferably, the second piston has a sidewall corresponding to the inner surface of the reservoir, and the second piston is slidably received in the inner surface of the reservoir.

More preferably, the shaft has a first end facing the exit opening of the reservoir, the second piston has an outer face, and wherein the first end of the shaft bears against the outer face of the piston.

More preferably, the device further comprises means for locking the second piston to a predetermined location along the reservoir axis.

Preferably, the reservoir has an exterior surface, and the fourth opening defines a mating surface on the exterior surface, and wherein the shaft has a mating shank having a corresponding shape for bearing against the mating surface.

Preferably, the inner face of the second piston is in substantial sealing connection with the inner surface of the reservoir.

Preferably, the device further comprises a compression spring having a first end, wherein the second piston has an outer face, and the first end of the spring bears against the outer face of the second piston. This describes a spring-loaded plunger.

Preferably, the reservoir comprises first and second end portions, the exit opening of the reservoir is disposed in the first end portion of the reservoir, and a fourth opening is disposed in the second end portion of the reservoir, the device further comprising a shaft axially disposed within the reservoir and slidably received in the backside opening. This allows the plunger to be pulled back.

Preferably, the compression spring defines an inner tube, and the shaft is axially disposed within the inner tube of the compression spring. This allows the plunger to be pulled back under resistance.

Preferably, the shaft has a first end facing the exit opening of the reservoir, the second piston has an outer face, and wherein the first end of the shaft bears against the outer face of the piston. This allows the piston to be pulled back under resistance.

Preferably, the device further comprises a locking pin comprising a tyne, wherein the reservoir has a transverse hole for receiving the tyne, the second piston has a sidewall having a recess shaped for receiving the tyne, and the tyne is inserted through the reservoir hole and is received within the recess of the second piston.

In accordance with the fourth embodiment (which requires a radially movable mixing element), it is preferred that the mixing element is axially movable, more preferably is unconstrained within the reservoir. Most preferably, the mixing element comprises a sphere.

In accordance with the fifth embodiment (which requires means for preventing back flow), it is preferred that the means comprises a check valve located near the exit opening in the injection chamber, the check valve biased in a normally closed position sealing the exit opening of the injection chamber from fluid communication with the entry opening, the valve being openable in response to increased pressure within the injection chamber and recloseable upon reduction of the pressure increase below a predetermined level.

Preferably, the check valve is located in the exit opening of the injection chamber.

Preferably, the device further comprises a first piston disposed in the inner surface of the injection chamber and having an inner face, and a flow restrictor disposed within the inner surface of the injection chamber between the inner face of the first piston and the exit opening of the injection chamber, the restrictor comprising a slitted sheet normally disposed parallel to the inner face of the first piston, wherein the slitted sheet comprises flaps formed by slits, wherein said flaps are oriented towards the exit opening of the injection chamber in response to increased pressure from the direction of the first piston, and the flaps return to a position parallel to the inner face upon reduction of the increased pressure, thereby restricting backflow.

In accordance with the sixth embodiment (which provides discrete quantities of bone cement under high pressure), it is preferred that the means comprises means for occluding the fluid communication between the entry and exit openings of the injection chamber. Preferably, the integral means comprises means for moving the bone cement through the injection chamber. Preferably, the integral means comprises an impermeable first piston disposed within the inner surface of the injection chamber, the first piston being movable over the entry opening of the sterile inner surface of the injection chamber. Preferably, the first piston comprises an inner face facing the exit opening and a cylindrical surface extending from the inner face and facing the inner surface of the injection chamber. Preferably, the inner surface of the injection chamber is between 0.1 cc and 5cc.

In accordance with the seventh embodiment (which requires means for applying continuous pressure to the bone cement in the reservoir), it is preferred that the means comprises a compression spring having:

i) a first end facing the exit opening of the reservoir, and ii) a second end extending away from the exit opening of the reservoir and contacting the second end portion of the reservoir defining a location.

Preferably, the device further comprises a second piston disposed within the reservoir and having an inner face facing the exit opening of the reservoir.

Preferably, the inner face of the second piston is located between exit opening of the reservoir and the first end of the spring. Preferably, the second piston has an outer face contacting the first end of the spring. Preferably, the spring has a relaxed length, and wherein the relaxed length is no less than the distance between the exit opening of the reservoir and the location where the second end of the spring contacts the second end portion of the reservoir, thereby enabling the second piston to approach the exit opening. Preferably, the device further comprises a first piston disposed within the injection chamber, the first piston having an inner face which is movable from a location near the exit opening to a location in the first end portion of the injection chamber. This feature provides automatic refill of the injection chamber.

In accordance with the ninth embodiment, it is preferred that the first end portion of the lever is pivotally attached to the device.

In accordance with the tenth embodiment (which requires a means for creating a vacuum in the injection chamber), it is preferred that the device further comprises means for maintaining pressure within the reservoir. Preferably, the means for creating a vacuum comprises a first piston disposed within the inner surface of the injection chamber.

In accordance with the eleventh embodiment (which requires an O-ring), it is preferred that the device further comprises a first piston having a sidewall disposed within the inner surfaces of the injection chamber, wherein the O-ring is disposed between the sidewall and the inner surface of the injection chamber.

In many orthopaedic surgeries, a radiopaque compound such as barium or barium sulfate ($BaSO_4$) is conventionally added to the bone cement mixture so that the cement can be seen via an x-ray. Investigators have also reported adding barium sulfate and metallic powder to conventional bone cements in order to provide an identifiable contrast image to aid the surgeon during the vertebroplasty. See, e.g., Jensen et al., *AJNR* 18:1897–1904, November 1997. Preferably, the bone cement used in accordance with the present invention is polymer-based, more preferably acrylic-based. Conventional acrylic-based bone cements are made from mixing a powder mixture and a liquid component. Typically, about 40 g of the powder mixture is combined with about 20 ml of the liquid component. Jensen, supra, identifies slow setting Codman Cranioplastic™ as the bone cement most suitable for vertebroplasty, and reports mixing this cement with 1 g tungsten and 5–6 g barium sulfate to produce about 48 $cm^3$ of powder mixture. Since the conventional Cranioplastic powder mixture comprises about 30 g of powder, about 58.6 wt % of which is PMMA powder, the Jensen powder mixture comprises about 47–49 wt % PMMA and about 16.5–18.8 wt % contrast agent.

One problem associated with the straightforward adaptation of orthopaedic bone cement mixtures to vertebroplasty is that the radiopacity of these conventional cements appears to be insufficient. Without wishing to be tied to a theory, it is believed that the reason for the lower radiopacity of the conventional compositions (when used in vertebroplasty) is that a smaller amount (generally about 5–20 cc, more particularly 7–10 cc) of cement is used in vertebroplasty surgeries as compared to orthopaedic applications (40–100 cc), and so there are fewer barium sulfate particles providing contrast on the x-ray. In addition, in vertebroplasty, the bone cement is typically applied as a thin thread (as compared to the bulk application in conventional orthopaedic applications), and so it is more difficult to distinguish the material from its background. Lastly, conventional orthopaedic applications do not require as high a level of visualization as is required in vertebroplasty.

Therefore, in order to increase the radio-opacity of the bone cement mixture, the present inventors increased the barium sulfate concentration in the powder mixture from conventional levels (16.5–18.8 wt %) to novel levels (for vertebroplasty applications) of between 20 wt % and about 30 wt % $BaSO_4$, and tested the suitability of these mixtures for vertebroplastic procedures. In general, it was determined that the radiopacity of the cement became more and more desirable as the barium sulfate concentration was increased.

The results of handling characteristics and mechanical testing of these new materials are summarized in Table I below:

TABLE I

| | | | Comparative Examples | | | |
|---|---|---|---|---|---|---|
| $BaSO_4$ (wt %) | Dough Time (min) | Setting Time (min) | Comp. Strength (MPa) | 4-pt. Flex. Strength (MPa) | Flexural Modulus (MPa) | Tensile Strength (MPa) |
| 0 | 3:50 | 16:34 | 95.31 | 72.69 | 2602 | 39.23 |
| 16.67 | 4:03 | 17:15 | 87.52 | 49.08 | 2390 | 29.03 |
| 20.60 | 3:53 | 18:29 | 82.21 | 49.02 | 2388 | 34.19 |
| 25.37 | 4:09 | 19:45 | 87.56 | 44.93 | 2379 | 25.89 |
| 28.57 | 4:11 | 20:45 | 84.36 | 46.50 | 2462 | 24.64 |

In general, Table I reveals that, in the range of 20–40 wt % $BaSO_4$, the cement had sufficient radio-opacity and was mechanically sound. However, it was further observed that the shelf life of at least the 28 wt % embodiment of these above mixtures (represented as Run 1 below) was less than optimal for use in vertebroplasty. In particular, embodiments which were aged up to 6 months displayed significantly higher setting times than similar non-aged embodiments, thereby demonstrating that this embodiment possessed a short shelf-life. Accordingly, three additional formulations (Runs 2–4 below) of barium sulfate-containing bone cement were evaluated, and these approximate formulations are presented in Table II below:

TABLE II

| Run | Contrast Agent | Contrast Fraction | grain size $D_{50}$ | BPO |
|---|---|---|---|---|
| 1 | Barium Sulfate | ~28 wt % | ~1 um | free |
| 2 | Barium Sulfate | ~28 wt % | ~1 um | bound |
| 3 | Barium sulfate | ~28 wt % | ~10 um | free |
| 4 | Zirconia | ~20 wt % | ~8 um | free |

For the purposes of the present invention "contrast fraction" represents the fraction of contrast agent in the powder fraction after it has been mixed with other powders. "Grain size $D_{50}$" represents the median particle size of the contrast agent. In Table II, "Bound BPO" means that at least 50 wt % of the BPO in the powder mixture is bound to other non-BPO particles, and "Free BPO" means that less than 50 wt % of the BPO is bound. The results of the evaluations of these materials are presented in Table III below:

TABLE III

| | Stability | Variability in Set Time | Handling |
|---|---|---|---|
| Run 1 | Failed | Small | Inferior |
| Run 2 | Pass | Large | Inferior |
| Run 3 | Pass | Small | Superior |
| Run 4 | Pass | Large | Superior |

In sum, it was found that the mechanical and handling characteristics of the Run 2–4 materials were sufficient for use in vertebroplasty. In particular, mechanical and handling testing for different lots of Run 3 (Coarse 10 um $BaSO_4$) was undertaken, and the results thereof are presented below in Table IV:

TABLE IV

| BaSO$_4$ | Dough Time (min) | Setting Time (min) | Comp. Strength (MPa) | 4-pt. Flex. Strength (MPa) | Flexural Modulus (MPa) | Tensile Strength (MPa) |
|---|---|---|---|---|---|---|
| A | 2:48 | 18:10 | 83.35 | 52.0 | 2446 | 33.2 |
| B | 2:34 | 17:35 | 84.52 | 55.19 | 2315 | NT |
| C | NT | NT | 92.19 | 52.8 | 2458 | NT |
| D | 2:28 | 16:59 | NT | NT | NT | NT |

Comparison of Tables I and IV reveals that the coarse BaSO$_4$ embodiments of Table IV have substantially similar setting times, compressive strengths, flexural moduli, and tensile strengths; and a higher 4-point flexural strength than the 16.67 wt % embodiment in Table I whose wt % was in the range of contrast agents reported by Jensen.

Therefore, in accordance with the present invention, there is provided a process comprising the steps of:
 a) providing a powder mixture suitable for producing a bone cement, the powder mixture comprising between 20 wt % and about 40 wt % contrast agent (preferably, barium sulfate powder),
 b) mixing the powder mixture with a liquid component to form a viscous bone cement, and
 c) injecting the viscous bone cement into a vertebral body.

Preferably, the bone cements of the present invention are produced by mixing a powder and a liquid component. Typically, the liquid component precursor of the bone cement comprises a methylmethacrylate (MMA) monomer and a small amount (0.1–3 vol %) of a accelerator, such as dimethyl-p-toluidine (DmpT). Preferably, the MMA monomer comprises at least 80 volume percent (vol %) of the liquid component, more preferably at least 90 vol %. Typically, the powder component comprises a mixture of i) polymethylmethacrylate polymer (PMMA), ii) an optional copolymer-containing powder (such as PMMA/copolymer powder), iii) an initiator powder, such as benzoyl peroxide ("BPO"), and iv) contrast agent. Preferably, the PMMA powder comprises at least 50 wt % of the powder mixture (and preferably between 40 wt % and 70 wt %), and the copolymer-containing powder comprises between 1 wt % and 60 wt % of the powder mixture. The contrast agent can be present in an amount of between between 20 wt % and 35 wt %, more preferably between 25 wt % and 35 wt %, and is preferably fully crystalline BaSO$_4$. The initiator powder typically comprises between 0.1 wt % and 2 wt % of the powder component.

It appears that conventional teachings related to the weight fraction of contrast agent in bone cements do not appreciate the criticality of selecting higher levels of constrast agent for vertebroplastic applications. Jensen does not report any insufficiency of the radiopacity of the bone cement used therein. Although U.S. Pat. No. 4,791,150 ("Braden") reports producing bone cements with powder mixtures in which pharmaceutical grade barium sulfate comprises 5–50 wt % of the polymer powder, and U.S. Pat. No. 5,795,922 ("Demian") reports powder mixtures containing 5–30 wt % barium sulfate, each was concerned with conventional orthopaedic applications and not vertebroplasty. Although Combs et al., Clin. Orthop. Rel. Res. (145) November–December 1979, pp. 287–291, reports that bone cement mixtures made from powders having up to 60 wt % barium sulfate have adequate strength, Combs (which used Surgical Simplex P starting materials) was primarily concerned with orthopaedic applications and sought to reduce the temperature of the newly-made cement (by adding BaSO$_4$) in order to possibly avoid thermal necrosis. In contrast, investigators reporting on vertebroplasty applications do not appear to have noted any need to control thermal necrosis. Rather, it appears that adding BaSO$_4$ to bone cement for vertebroplasty would be discouraged by the conventional teachings of vertebroplasty, as it has been theorized that subjecting the spine area to high temperatures actually helps alleviate back pain by deadening nerve endings.

As noted in Table I, the four-point flexural strength of the comparative 16.67 wt % sample was about 30% lower than that of neat Cranioplastic™. Accordingly, it was believed that further additions of BaSO$_4$ to the powder mixture would produce larger and larger decreases in strength, finally leading to catastrophic breakdown. Surprisingly, it was found that the compressive and flexural strengths of the even higher barium sulfate mixtures of Table IV of the present invention were fairly equivalent to that of the comparative mixture using 16.67 wt % barium sulfate shown in Table I. Moreover, this finding that further barium sulfate additions will not compromise strength provides valuable new barium sulfate-cement compositions which have both the radioopacity and the mechanical strength required for vertebroplasty. Therefore, preferably, the barium sulfate concentration is between 20 and 40 wt %, more preferably between 25 and 35 wt %.

In addition, review of TABLE IV indicates that the increased BaSO$_4$ concentrations in the mixtures of the present invention yield longer setting times (about 18–20 minutes) than those of cements having lower contrast agent fractions, such as the 16.67 wt % embodiment of Table I (about 17¼ minutes). Long setting times are attractive for vertebroplastic bone cements because, in use, the cement must be able to suitably flow from the injection gun through a small tube to the vertebral body, and then refrain from leaking from the vertebral body once it is in place. Accordingly, a vertebroplastic cement should avoid setting for at least 10 minutes, and more preferably for much longer time periods such as 14–20 minutes, with some embodiments being in the range of 18–20 minutes. Most conventional orthopaedic barium sulfate-containing bone cements typically have setting times on the order of 8–12 minutes, and so are inadequate for this application. Combs reported setting times of no more than only 15 minutes, albeit at an ambient temperature of about 30° C. Without wishing to be tied to a theory, it is believed that the reason for Jensen's selection of "slow setting" Cranioplastic as the base material for a vertebroplastic cement could have been this long setting time feature. However, TABLE I indicates that the 16.5–18.8 wt % mixtures described by Jensen probably had setting times of about 17¼ minutes.

Therefore, also in accordance with the present invention, there is provided a method of using a bone cement, comprising the steps of:
 a) providing a bone cement having a setting time of at least 18 minutes (preferably, between 18 and 20 minutes), and
 b) injecting the bone cement into a vertebral body.

Preferably, the bone cement is made from a formulation comprising a powder component comprising between 20 wt % and 40 wt % contrast agent, preferably BaSO$_4$.

It is believed that at least another reason for the long setting times of these preferred formulations may be the low level of initiator powder. Without wishing to be tied to a theory, it is believed that the amount of initiator has a significant effect upon the setting time of the bone cement, with higher levels of initiator producing lower setting times. Accordingly, in some embodiments, the powder component of the bone cement has not only a large amount of contrast agent (to provide the radio-opacity desirable in vertebroplasty, but also a low level of initiator powder (to provide the large setting times desirable in vertebroplasty). Therefore, preferably, the bone cement used in accordance with this embodiment of the present invention is made with a formulation comprising a powder component having:
   a) between 20 and 40 wt % contrast agent and
   b) no more than 1.1 wt % initiator powder.

Preferably, the initiator powder comprises no more than 1.0 wt %, more preferably no more than 0.75 wt %, most preferably no more than 0.5 wt % of the powder component. Preferably, the initiator powder is benzoyl peroxide. Preferably, the contrast agent is $BaSO_4$.

Alternatively, setting times may be increased by limiting the amount of accelerator (DmpT) in the liquid component of the bone cement. Without wishing to be tied to a theory, it is believed that the amount of liquid accelerator has a significant effect upon the setting time of the bone cement, with higher levels of accelerator producing lower setting times. Accordingly, in some embodiments, the bone cement has not only a large amount of contrast agent in the powder component (to provide the radio-opacity desirable in vertebroplasty), but also a low level of liquid accelerator (to provide the large setting times desirable in vertebroplasty). Preferably, the accelerator is DmpT. Therefore, in accordance with the present invention, there is provided a bone cement formulation comprising:
   a) a liquid component comprising no more than 2.4 vol % accelerator, and
   b) a powder component comprising between 20 wt % and 40 wt % contrast agent.

Preferably, the liquid component comprises no more than 1.5 vol % accelerator, more preferably no more than 1 vol % accelerator, most preferably between 0.52 vol % and 0.82 vol %. Preferably, the accelerator is DmpT. Preferably, the contrast agent is $BaSO_4$.

When compared to the formulations of Combs having large amounts of contrast agents, the ratio of DmpT/BPO in the formulations of the present invention is low. This condition is advantageous because, according to Kuhn, "A surplus of BPO may favor complete turnover of DmpT. A surplus of DmpT, however, results in almost total consumption of the BPO, leaving a high residue of DmpT in the cement." Complete turnover of DmpT is desirable because DmpT is considered by the literature to be toxic. Thus, the present invention provides both the low level of BPO desirable for setting and injection times suitable for vertebroplasty and a low DmpT/BPO ratio desirable for minimizing residual DmpT.

Therefore, in accordance with the present invention, there is provided a bone cement formulation comprising:
   a) a powder component comprising between 20 wt % and 40 wt % contrast agent and an initiator present in an amount defining a powder initiator fraction, and
   b) a liquid component comprising an accelerator present in an amount defining a liquid accelerator fraction, wherein the ratio of the liquid accelerator fraction to the powder initiator fraction is less than 1.75.

For the purposes of the present invention, the liquid accelerator fraction is determined on a volumetric basis, while the powder initiator fraction is determined on a weight basis.

Similarly, in accordance with the present invention, there is provided a bone cement formulation comprising:
   a) a powder component comprising between 20 wt % and 40 wt % contrast agent and an initiator present in an amount defining a powder initiator fraction, and
   b) a liquid component comprising an accelerator present in an amount defining a liquid accelerator fraction, wherein the ratio of the liquid accelerator fraction to the powder initiator fraction is between 1.3 and 1.9, and wherein the powder initiator fraction is less than 1.3%.

Similarly, in some embodiments having the above high levels of contrast agent, the accelerator (preferably, DmpT) level is less than 2.6 vol % and the accelerator/initiator (preferably, DmpT/BPO) ratio is between 1.67 and 1.99. In some embodiments, the accelerator (preferably, DmpT) level is less than 1.9 vol % and the accelerator/initiator (preferably, DmpT/BPO) ratio is between 1 and 2. These embodiments provide both controlled amounts of initiator (preferably, BPO) and accelerator (preferably, DmpT) needed for producing the desired setting and injection times, while minimizing the accelerator (preferably, DmpT) level.

Additional data were obtained for Runs A, B and D in Table IV, and these data are presented in TABLE V. An "Injection time" represents the window of time during which the cement can be extruded. The injection time should be at least 10 minutes in duration in order to be advantageous for use in vertebroplasty applications. In order to determine the injection time of a particular formulation, the powder and liquid are mixed (at which time the "injection time" window begins), and the mixed cement is then extruded at 23° C. through an 11 gauge biopsy needle using a 1 ml syringe. This procedure is then repeated every 30 seconds until the cement becomes too difficult to further extrude through the syringe and needle. The full procedure is then repeated with another sample from the same batch, and the mean time of the two samples is obtained. Preferably, the injections times results should be within 30 seconds of each other.

The Exotherm tests were performed in accordance with ASTM F451-99a.

TABLE V

| | Injection Time (minutes) | Exotherm |
|---|---|---|
| Run A | 12:15 | 67.0° C. |
| Run B | 11:00 | 62.7° C. |
| Run C | — | — |
| Run D | 10:35 | — |

Evaluation of the data of Table V in light of the specifications provided above indicate that the formulations of the present invention provide injection times suitable for use in vertebroplasty. The exotherms are relatively low when compared to conventional bone cements.

In addition, three other formulations of the present invention were likewise subjected to injection time and exotherm testing. These formulations yielded injections times between 10:25 and 10:39 (minutes:seconds), with exotherms of between 59.7° C. and 63.0° C. These results demonstrate the consistency of the formulations of the present invention in providing these properties.

Therefore, in accordance with the present invention, there is provided a process comprising the steps of:

a) providing a powder mixture suitable for producing a bone cement, (preferably, the powder mixture comprising between 20 wt % and about 40 wt % contrast agent),
b) mixing the powder mixture with a liquid component to form a viscous bone cement, and
c) injecting the viscous bone cement into a vertebral body, wherein at least a portion of the injection step occurs at least 10 minutes (preferably at least 11 minutes) after the mixing step.

As noted in Tables III and IV above, it was found in Run 3 that adjusting the grain size of the barium sulfate powder so that the average grain size ($D_{50}$) was 10 um resulted in a bone cement mixture having not only sufficient radiopacity and mechanical strength, but also sufficient shelf life, handling and bio-compatibility. Without wishing to be tied to a theory, it is believed that intergranular reaction between $BaSO_4$ and BPO leads to degradation and/or inactivation of the BPO, and that increasing the amount of $BaSO_4$ in the powder mixture accelerates the inactivation/degradation. It is further believed that the increased level of degradation/ inactivation was responsible for the poor shelf life of the mixture (as lower BPO levels led to longer setting times) and for the biocompatability problems as well (as lower BPO levels led to higher levels of unreacted DmpT in the cement). When the barium sulfate particle size was increased, the relative surface area of the $BaSO_4$ significantly decreased, thereby reducing the interfacial area for $BaSO_4$-BPO interaction, thereby limiting and/or eliminating the degradation/ inactivation of BPO. The high radiopacity of this material is surprising because it was thought that increasing the $BaSO_4$ particle size would dehomogenize the mixture, thereby reducing the radiopaque distinctiveness of the mixture. However, it was found that the radiopacity was still sufficient. It is believed that the higher content of $BaSO_4$ present in the mixtures of the present invention provides the sufficient radiopacity without requiring the homogeneity afforded by using fine $BaSO_4$.

A review of conventional bone cement literature appears to indicate that barium sulfate has been present in these cements only as very fine grains. For example, U.S. Pat. No. 5,512,610 ("Lin") discloses the use of 1 $\mu$m barium sulfate, and noted that this powder produced stress risers within the cement. Demian teaches that the typical radiopacifier particle size is less than 1.5 $\mu$m and most are less than 1 $\mu$m. Although U.S. Pat. No. 6,080,801 ("Draenert") discloses 5–15 $\mu$m "particles" of barium sulfate, Draenart also provides a picture (in FIG. 1 thereof) of such a particle which indicates that the barium sulfate particle is really an agglomerate of near-colloidal submicron-sized grains. Draenart also noted that conventional barium sulfate particles tended to "conglomerate" and suggested partially embedding these particles with the PMMA polymer powder. Likewise, Kuhn, "Bone Cements", Springer (2000) at page 245, teaches 20–150 $\mu$m size barium sulfate "particles" but likewise provides a picture (in FIG. 8b thereof) which indicates that such particles are really an agglomerate of near-colloidal submicron-sized grains. Lastly, Jensen, supra, noted that conventional barium sulfate powder needed to be crushed prior to use—an indication that agglomerates were similarly present. Accordingly, the literature does not teach the use of coarse (>2 $\mu$m) barium sulfate grains in bone cements. For the purposes of the present invention, a "grain" is a non-porous, typically crystalline mass, while a "particle" can include an agglomeration of grains.

Accordingly, Applicants have discovered that using coarse (>2 um) barium sulfate grains not only solves the problem of satbility, but also provides sufficient contrast capability and periphery detection precision necessary for use in vertebroplasty.

In addition, further review of Table II reveals that both the handling and set time variance of this coarse grain embodiment (Run 3) were superior to other novel formulations (Runs 2 & 4) which provided acceptable shelf life.

Therefore, in accordance with the present invention, there is provided a powder mixture for producing bone cement, the mixture comprising contrast agent grains (preferably, barium sulfate grains) having a $D_{50}$ grain size of at least 3 $\mu$m, more preferably at least 5 $\mu$m, and most preferably at least 10 $\mu$m. In some embodiments, the $D_{50}$ grain size is between 6 and 14 $\mu$m. These coarse grain embodiments provide particular advantage to high $BaSO_4$-containing powder mixtures, such as those powder mixtures comprising between 20 wt % and 40 wt % $BaSO_4$ in that the coarse grains do not form strength-degrading agglomerates. Preferably, the $BaSO_4$ grains are not embedded (within the PMMA powder. In preferred embodiments of powder mixtures containing coarse, high wt % $BaSO_4$ powder, more than 50 wt % of the BPO is unbound or "free" (preferably, at least 75 wt %). Free BPO is advantageous over bound BPO in that it can more quickly initiate the bone cement polymerization reaction, and so help adjust desired setting times.

It is further noted that the 4-point flexural strength of Run 3 (which used coarse $BaSO_4$) is superior to that of the 28.57 wt % embodiment of Table I (which used fine $BaSO_4$). Without wishing to be tied to a theory, it is believed that because the coarse grains are unagglomerated, they do not produce intergranular porosity and so do not diminish strength as much as fine $BaSO_4$. Therefore, also in accordance with the present invention, there is provided a powder mixture suitable for producing bone cement, the powder mixture comprising between 20 wt % and 40 wt % barium sulfate powder, wherein the barium sulfate powder grains are unagglomerated.

Also as noted in Table II, it was further found that the shelf life of the high barium sulfate mixtures could be sufficiently enhanced without changing particle size simply by replacing the free benzoyl peroxide of Run 1 with bound benzoyl peroxide. Without wishing to be tied to a theory, it is believed that intergranular interaction between free BPO grains and high levels of $BaSO_4$ grains cause BPO degradation/inactivation, thereby extending setting times. BPO grains bound within PMMA grains are shielded from this interaction and so do not degrade. Although the high-$BaSO_4$ bone cement of Combs is also made via bound BPO, it contains only about 15 wt % PMMA and 75 wt % PMMA-styrene copolymer, and so is characterized by a large co-polymer fraction. Without wishing to be tied to a theory, it is believed that co-polymers powders can more readily absorb the liquid monomer component than single polymer powders such as PMMA. It is further believed that co-polymer powders more easily solubilize in the liquid component than do single polymer powders. Because of their ready absorbability and solubility, the addition of co-polymer powders tend to produce an increased reaction rate and therefore more quickly increase the viscosity of the bone cement. In contrast, the powder mixture of the present invention comprises at least 40 wt % PMMA powder and only about 14 wt % copolymer. It is believed the low co-polymer content of this embodiment will not increase the viscosity of the bone cement as quickly. This may be a desirable property in vertebroplasty applications.

Therefore, in accordance with the present invention, there is provided a powder mixture suitable for use as a bone cement, the powder mixture comprising:
a) between 20 wt % and 40 wt % contrast agent (preferably, barium sulfate),
b) no more than 50 wt % co-polymer.

Preferably, the copolymer comprises no more than 35 wt % of the powder mixture, more preferably, no more than 20 wt %. Preferably, the powder mixture further comprises c) initiator powder, wherein the initiator powder is bound within the PMMA powder. Preferably, the initiator powder comprises benzoyl peroxide ("BPO"). The combination of low copolymer content and bound BPO provides the low setting times and stability desired for high contrast agent formulations.

Table IV reveals that two Runs (Runs 3 & 4) which have acceptable shelf life and biocompatability despite the use of free BPO. Although bound BPO is advantageous in some situations, there are likewise some situations in which fast-initiating free BPO is desirable. Therefore, also in accordance with the present invention, there is provided a powder mixture suitable for producing a bone cement, the powder mixture comprising between 20 wt % and 40 wt % barium sulfate (preferably, between 20 wt % and 40 wt % contrast agent (preferably, $BaSO_4$) and free initiator powder. Preferably, the initiator is benzoyl peroxide ("BPO"). This powder mixture has an advantage over conventional low-$BaSO_4$ mixtures in that it has sufficient contrast agent for use in vertebroplasty, and it has an advantage over the high-$BaSO_4$, BPO-bound mixture of Combs in that its free BPO can quickly initiate the polymerization reaction. Lastly, it has an advantage over other powder mixtures containing free BPO, such as Palacos-R and Cerafix, in that these mixture contain 9–15 wt % zirconia and so suffer from potential low radiopacity and abrasion problems.

Next, it was further found that replacing barium sulfate with zirconia grains in the powder mixture also produced a bone cement mixture having sufficient radio-opacity and shelf life. In particular, one cement of the present invention containing about 20 wt % monoclinic zirconia was found to have the following mechanical properties:

| | |
|---|---|
| Compressive strength | 83.25 MPa |
| Flexural Strength | 64.31 MPa. |

Review of these results against those for $BaSO_4$-based cements presented earlier reveals that the zirconia-based cements have a superior flexural strength. Without wishing to be tied to a theory, it is believed the superior flexural strength of the zirconia-based cements is due to the lower volume occupied by the zirconia. Zirconia is both more radiopaque and heavier (each on a gram-for-gram basis) than barium sulphate and therefore less of it is required to achieve the same level of radiopacity. Since it is believed that the volume of added contrast agent affects the mechanical properties of the cement, and since zirconia occupies significantly less volume than barium sulphate, it is believed the mechanical properties of the cement will be superior.

Therefore, in accordance with the present invention, there is provided a powder mixture suitable for producing a bone cement, the powder mixture comprising between 16 wt % and 40 wt % free zirconia powder (preferably, between 18 wt % and 30 wt %). Preferably, the mixture further comprises no more than 50 wt % copolymer. Preferably, the powder mixture further comprises benzoyl peroxide ("BPO"). More preferably, the BPO is free.

In some embodiments, the precursor materials for the bone cement are as follows:

The powder comprises:

| Component | Approximate Fraction |
|---|---|
| Methyl methacrylate polymer | 56.8 parts w/w |
| Methyl methacrylate-styrene copolymer | 14.2 parts w/w |
| Free Benzoyl Peroxide | 0.4 parts w/w |
| Free Barium Sulfate($D_{50}$ ~ 10 um) | 28.6 w/w, |

And the liquid precursor component comprises:

| | |
|---|---|
| Methyl methacrylate monomer | 95.05 parts v/v |
| Ethylene dimethacrylate monomer | 4.28 parts v/v |
| Dimethyl-p-toluidine | 0.67 parts v/v |
| Hydroquinone | 20 +/− 5 ppm |
| 4-methoxyphenol | 12 ppm. |

It was further found that when about 9–12 ml of the above-cited liquid mixture is first added to the reservoir, and then about 22–30 g of the above-cited powder mixture is added thereto, the resulting formulation could be suitably mixed by simple hand-controlled shaking of the combined mixtures when a 0.625 inch diameter metal ball in a 40–66 cc tube is also placed in the reservoir. In particular, the mixture was thoroughly homogenized and had a viscosity suitable for injection after only 10–30 seconds of ball mixing. This discovery allows for a drastically simplified injection device design, wherein the mixing shank in the reservoir is completely replaced by a freely movable mixing element. Preferably, the reservoir has a long thin tubular shape adapted to promote uniform mixing. More preferably, the ratio of the reservoir cross-section to the useful reservoir length is no more than 1 $cm^2$/cm. The mixing element may have any shape but is preferably either a ball or cylinder, and preferably has a diameter of at least one-half (½) that of the reservoir diameter. In one preferred embodiment, the ratio of the useful reservoir length to the reservoir cross section is less than 0.75 $cm/cm^2$.

Now referring to FIG. 9a, there is provided an injection device 1 wherein freely movable mixing element 201 is housed within reservoir 3. Once the reservoir piston has been spring loaded, the precursor materials and mixing element 201 have been loaded into reservoir 3, and threads 184 of reservoir cap 182 have been threadably received upon the corresponding thread 185 (to produce FIG. 9a), the device 1 is simply hand shaken for about one-half minute to produce a bone cement having a viscosity suitable for injection. Next, rod 203 is rotated 90 degrees, thereby allowing shoulder (not shown) to pass through hole 207 and releasing spring 209.

Therefore, in accordance with the present invention, there is provided an apparatus for producing bone cements having a low viscosity, comprising:
a) a mixing reservoir,
b) a powder precursor (preferably PMMA) for producing bone cement housed within the reservoir,
c) a liquid precursor (preferably MMA) for producing bone cement housed within the reservoir, and d) a freely movable mixing element housed within the reservoir.

In preferred embodiments, and now referring to FIG. 9a, there is provided an injection device for injecting bone cement, comprising:
a) a reservoir 3 having an exit opening 5,
b) an injection chamber 21 for injecting the bone cement, the chamber having a sterile inner surface 23 forming entry 25 and exit 27 openings, the entry opening of the sterile inner surface of the injection chamber being in fluid communication therebetween,
c) a first piston 33 housed within the injection chamber and having an inner face 35 facing the exit 27 opening of the injection chamber, and
d) a freely movable mixing element 201 housed within the reservoir 3.

The device of the present invention is suitable for delivering injectable biomaterials, and for injecting bone cement in particular.

Also in accordance with the present invention, there is provided a method of injecting a bone cement into an interior region of a vertebral body, comprising the steps of:
a) providing a vertebroplasty injection device having an injection chamber and a reservoir in fluid connection therewith, the injection chamber and the reservoir each containing the bone cement,
b) fluidly connecting the injection chamber to the interior region of the vertebral body,
c) discretely injecting a first amount of bone cement from the injection chamber into the interior region of the vertebral body,
d) flowing bone cement from the reservoir to the injection chamber, and
e) discretely injecting a second amount of bone cement from the injection chamber into the interior region of the vertebral body.

Preferably, each amount of bone cement is between 0.1 cc and 5 cc (preferably between 0.5 cc and 2 cc).

We claim:
1. A device for injecting bone cement, comprising:
a) a reservoir having an exit opening,
b) an injection chamber having:
   i) first and second end portions, and
   ii) a sterile inner surface forming an entry opening in the first end portion and an exit opening in the second end portion,
the exit opening of the reservoir and the entry opening of the sterile inner surface of the injection chamber being in fluid communication therebetween, and
wherein the injection chamber inner surface defines a volume of between 0.1 and 0.5 cc,
c) a second piston housed within the reservoir and having an inner face facing the exit opening of the reservoir, and
d) a locking pin comprising a tyne,
wherein the reservoir has a transverse hole for receiving the tyne, the second piston has a sidewall having a recess shaped for receiving the tyne, and the tyne is inserted through the reservoir hole and is received within the recess of the second piston.

* * * * *